United States Patent [19]

Hirai et al.

[11] Patent Number: 5,187,209
[45] Date of Patent: Feb. 16, 1993

[54] COLLOIDAL METAL DISPERSION, AND A COLLOIDAL METAL COMPLEX

[76] Inventors: Hidefumi Hirai, 14-10, Yutenji 1-chome, Meguro-ku; Makoto Komiyama, 16-1-508, Kosuge 4-chome, Katsushika-ku, both of, Tokyo; Michitaka Otaki, Oimatsu Jyutaku 3-403, 30 Oimatsu-cho, Nishi-ku, Yokohama-shi, Kanagawa-ken, all of Japan

[21] Appl. No.: 745,978

[22] Filed: Aug. 12, 1991

Related U.S. Application Data

[60] Continuation of Ser. No. 395,821, Oct. 6, 1989, abandoned, which is a division of Ser. No. 46,608, May 7, 1987, Pat. No. 4,888,248.

[30] Foreign Application Priority Data

| Jul. 1, 1986 | [JP] | Japan | 61-152761 |
| Jul. 8, 1986 | [JP] | Japan | 61-158676 |
| Jul. 24, 1986 | [JP] | Japan | 61-172781 |
| Jul. 24, 1986 | [JP] | Japan | 61-172782 |
| Aug. 15, 1986 | [JP] | Japan | 61-190435 |
| Aug. 15, 1986 | [JP] | Japan | 61-190436 |
| Dec. 17, 1986 | [JP] | Japan | 61-298835 |
| Dec. 17, 1986 | [JP] | Japan | 61-298836 |
| Dec. 17, 1986 | [JP] | Japan | 61-298837 |
| Dec. 17, 1986 | [JP] | Japan | 61-298838 |
| Dec. 17, 1986 | [JP] | Japan | 61-298839 |
| Dec. 17, 1986 | [JP] | Japan | 61-298840 |

[51] Int. Cl.$^5$ .............. A61K 47/00; C08K 9/10; C12N 11/14
[52] U.S. Cl. .............. 523/205; 427/214; 427/216; 427/221; 424/1.1; 428/403; 428/407; 252/313.1; 523/206; 523/375; 524/501
[58] Field of Search .............. 427/214, 216, 221; 428/403, 407; 523/205, 206, 375; 524/501; 424/1.1; 252/313.1

[56] References Cited

U.S. PATENT DOCUMENTS

| 4,206,094 | 6/1980 | Yen et al. | 523/205 |
| 4,219,411 | 8/1980 | Yen et al. | 209/13 |
| 4,888,248 | 12/1989 | Hirai et al. | 523/205 |

*Primary Examiner*—Herbert J. Lilling
*Attorney, Agent, or Firm*—Armstrong, Westerman, Hattori, McLeland & Naughton

[57] ABSTRACT

Thers is disclosed a novel colloidal metal dispersion in which colloidal particles of a metal are protected by specific polymers including hydrazide polymers, acrylic ester polymers and acrylamide polymers. The colloidal metal dispersion is highly stable, and the colloidal metal particles protected by such specific polymers can be easily and strongly bound to various amino group-containing compounds to give stable colloidal metal complexes, which have a wide variety of uses, such as the use as a solid catalyst, the use for the treatment and diagnosis of various diseases, the use for studying tissues of living bodies, the use for inducing mutation of microorganisms, etc.

6 Claims, 1 Drawing Sheet

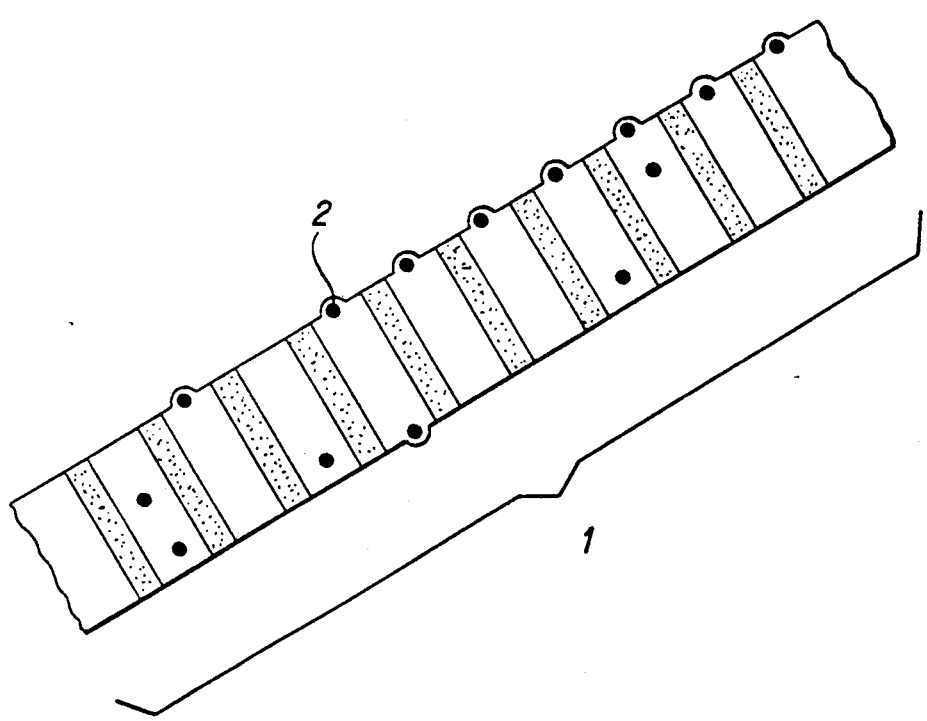

COLLOIDAL METAL DISPERSION, AND A COLLOIDAL METAL COMPLEX

This application is a continuation of application Ser. No. 395,821, filed on Oct. 6, 1989 now abandoned, which is a division of Ser. No. 046,608, filed on May 7, 1989, now U.S. Pat. No. 4,888,248.

BACKGROUND OF THE INVENTION

1. Field Of The Invention

The present invention relates to a colloidal metal dispersion, a colloidal metal complex and a process for the preparation of a colloidal metal complex. More particularly, the present invention is concerned with a colloidal metal dispersion in which colloidal particles of a metal are protected by a specific polymer, and with a colloidal metal complex comprising an amino group-containing compound and colloidal particles of a metal bound thereto through a specific protective polymer adsorbed on said colloidal particles. Further, the present invention is concerned with a process for the preparation of a colloidal metal complex. The colloidal particles of a metal in the colloidal metal dispersion of the present invention are readily bound to an amino group-containing compound to give a stable colloidal metal complex, which is not only useful as, e.g. a solid catalyst for various reactions, but also can be advantageously used for the study of living bodies and for the treatment and diagnosis of various diseases.

2. Discussion Of Related Art

It is well known that by the addition of gelatin to a colloidal gold dispersion, the dispersion becomes so stable due to the protective action of the gelatin that the colloidal gold can, for example, be dried without undergoing any change in color. Those which exert such protective action are called protective colloids. Besides gelatin, well-known as protective colloids are natural high molecular weight compounds, such as albumin, gum arabic, protalbinic acid and lysalbinic acid. In addition, it has been reported that some synthetic polymers, for example, polyvinylpyrrolidone, polyvinyl ether and polymethyl vinyl ketone act as protective colloids and that when a metallic ion solution is subjectd to reduction in the presence of these synthetic polymers, there is obtained a colloidal dispersion of fine particles of the metal protected by the polymers and the thus obtained colloidal metals can be used, for example, as catalysts (see e.g., "Industrialization of Polymer Catalysts" pp 151-179(1981)) publish by CMC Co., Ltd., Japan.

However, such known colloidal dispersions in which colloidal metals are protected by natural or synthetic polymers as mentioned above have problems. That is, colloidal dispersions in which the colloidal metal is protected by natural polymers, such as gelatin, have a drawback that they are instable and are not reproducible in respect of particle size distribution of colloidal metals. In the case of the colloidal dispersions in which colloidal metals are protected by the above-mentioned kinds of synthetic polymers, the reactivity of the synthetic polymers is low and, hence, it is difficult to strongly bind the colloidal metals to various substances. Therefore, the use of colloidal dispersions in which the above-mentioned synthetic polymers are used as protective polymers is limited, for example, to only the preparation of a catalyst for the hydrogenation of olefins.

SUMMARY OF THE INVENTION

The present inventors have made extensive and intensive studies with a view to developing a colloidal dispersion of a metal which is not only stable but also can be strongly bound to various substances for use in various fields in which the known colloidal metals cannot be practically used. As a result, they have found that specific polymers including hydrazide polymers, acrylic ester polymers and acrylamide polymers exhibit an excellent protective action on a colloidal metal, and that colloidal metals protected by such specific polymers can be easily and strongly bound to various amino group-containing compounds to give stable colloidal metal complexes, which have a wide variety of uses, such as the use as a solid catalyst, the use for the treatment and diagnosis of various diseases, the use for studying tissues of living bodies and the use for inducing mutation of microorganisms.

It is, therefore, an object of the present invention to provide a novel highly stable colloidal metal dispersion in which the colloidal metal particles are protected by a specific polymer.

It is another object of the present invention to provide a novel colloidal metal complex comprising an amino group-containing compound having bound thereto colloidal metal, which can be advantageously utilized in various fields.

It is a further object of the present invention to provide a method for the preparation of the novel colloidal metal complex.

The foregoing and other objects, features and advantages of the present invention will be apparent from the following detailed description and appended claims taken in connection with the accompanying drawing in which:

BRIEF DESCRIPTION OF THE DRAWING

The drawing is a diagrammatic illustration of an electron photomicrograph (×307,500) of tropomyosin which is bonded with a troponin-bound colloidal platinum of the present invention, from which the state of bonding in the rabbit body between tropomyosin and troponin can be studied.

DETAILED DESCRIPTION OF THE INVENTION

In one aspect of the present invention, there is provided a polymer-protected colloidal metal dispersion comprising:

(a) a dispersion medium;

(b) colloidal particles of at least one metal selected from the group consisting of metals belonging to Groups Ib, VIIb and VIII of the Periodic Table, said colloidal particles being dispersed in said dispersion medium; and (c) a protective polymer adsorbed on said colloidal particles;

said protective polymer comprising 1 to 100 mol percent, based on the total of units (i), (ii) and (iii), of units (i) represented by the formula [I]

wherein

R[1] is selected from the group consisting of a hydrogen atom, a substituted or unsubstituted alkyl group having 1 to 6 carbon atoms, a substituted or unsubstituted phenyl group, a hydroxyl group,

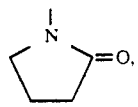

—CO—R and —O—R',
wherein

R is selected from the group consisting of a substituted or unsubstituted alkyl group having 1 to 10 carbon atoms and —$(CH_2)_{n1}$—$X_{n2}$—$(CH_2)_{n3}$—$Y_{n4}$—$(CH_2)_{n5}$—CO—$R^7$,
wherein X and Y are each independently selected from the group consisting of —O— and —NH—, R[7] is selected from the group consisting of —NH—NH$_2$, —A—R[8] and —NH$_2$,
wherein A is selected from the group consisting of —O— and —S—, and R[8] is selected from the group consisting of a substituted or unsubstituted alkyl group having 1 to 10 carbon atoms, a substituted or unsubstituted phenyl group and a substituted or unsubstituted succinimido group, n1, n3 and n5 each independently represent an integer of 0 to 6, and n2 and n4 each independently represent an integer of 0 or 1, and R' has the same meaning as R, and R[2] represents —$(CH_2)_{n1'}$—$X'_{n2'}$—$(CH_2)_{n3'}$—$Y'_{n4'}$—$(CH_2)_{n5'}$—CO—R[7']
wherein X', Y', R[7'], n1', n2', n3', n4' and n5' respectively have the same meanings as X, Y, R[7], n1, n2, n3, n4 and n5; 0 to 99 mol percent, based on the total of units (i), (ii) and (iii), of units (ii) represented by the formula [II]

wherein

R[3] is selected from the group consisting of a hydrogen atom, a substituted or unsubstituted alkyl group having 1 to 6 carbon atoms, a substituted or unsubstituted phenyl group, a hydroxyl group,

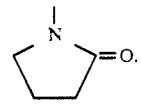

—CO—R and —O—R'
wherein

R and R' are as defined above, and

R[4] represents —$(CH_2)_{n1''}$—$X''_{n2''}$—$(CH_2)_{n3''}$—$Y''_{n4''}$—$(CH_2)_{n5''}$—CO—R[9]
wherein X'', Y'', n1'', n2'', n3'', n4'' and n5'' respectively have the same meanings as X, Y, n1, n2, n3, n4 and n5, and R[9] represents —A'—R[10],
wherein A' has the same meaning as A, and R[10] is selected from the group consisting of a hydrogen atom, an alkali metal, an alkaline earth metal, a substituted or unsubstituted alkyl group having 1 to 10 carbon atoms, a substituted or unsubstituted phenyl group and a substituted or unsubstituted succinimido group; and 0 to 99 mol percent, the total of units (i), (ii) and (iii), of units (iii) represented by the formula [III]

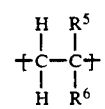

wherein

R[5] is selected from the group consisting of a hydrogen atom, a substituted or unsubstituted alkyl group having 1 to 6 carbon atoms, a substituted or unsubstituted phenyl group, a hydroxyl group,

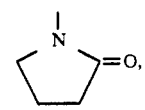

—CO—R and —O—R'
wherein

R and R' are as defined above, and

R[6] is selected from the group consisting of a hydroxyl group,

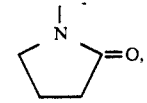

—CO—R and —O—R'
wherein

R and R' are as defined above;
provided that where R[1] is a hydrogen atom, R[2] is —CO—NH$_2$ and the proportion of units (ii) is 0 mol percent, R[6] is selected from the group consisting of a hydroxy group, —CO—R and —O—R';

where R[7] is —NH—NH$_2$, the —NH—NH$_2$ groups are unmodified, or part or all of the —NH—NH$_2$ groups are modified to form —N$_3$ groups; and where R[1] is hydrogen atom or a substituted or unsubstituted alkyl group having 1 to 6 carbon atoms, the proportions of units (i), (ii) and (iii) are respectively 1 to 95 mol percent, 0 to 90 mol percent and 5 to 99 mol percent, the total of units (i), (ii) and (iii).

The colloidal particles in the colloidal metal dispersion of the present invention is of at least one metal selected from the group consisting of the metals belonging to Groups Ib, VIIb and VIII of the Periodic Table. Preferred examples of the metal include gold, silver, platinum, ruthenium, rhodium, palladium, osmium, rhenium, iridium, copper and nickel. Further, the metal may be radioactive, that is, radioactive gold, radioactive silver and radioactive platinum and the like may be employed.

The terminology "colloidal metal dispersion" used herein means a system comprising a dispersion medium, such as water and an alcohol, and, dispersed therein, fine metallic particles having a diameter of about 5 to 1000 Å.

In the colloidal metal dispersion of the present invention, colloidal particles of at least one metal have adsorbed thereon the above-mentioned specific protective polymer and are protected by the protective polymer. In the colloidal particles protected by the protective polymer according to the present invention, the colloidal particles are sufficiently stabilized by the protective polymer, so that no precipitate is formed even after the colloidal dispersion is subjected to centrifugation, for example, at 5000 rpm for 10 minutes. As mentioned above, the protective polymer is adsorbed on the colloidal particles. However, part of the protective polymer may not be adsorbed on the colloidal particles and dissolved in the dispersion medium.

The protective polymer in the colloidal metal dispersion of the present invention comprises 1 to 100 mol percent, based on the total of units (i), (ii) and (iii), of units (i) represented by the formula [I], 0 to 99 mol percent, based on the total of units (i), (ii) and (iii), of units (ii) represented by the formula [II], and 0 to 99 mol percent, based on the total of units (i), (ii) and (iii), of units (iii) represented by the formula [III]. Preferably, the protective polymer comprises 10 to 50 mol percent of the units (i), 0 to 50 mol percent of the units (ii), and 30 to 90 mol percent of the units (iii), based on the total of units (i), (ii) and (iii).

In the formula [I]

[I]

$R^1$ is selected from the group consisting of a hydrogen atom, a substituted or unsubstituted alkyl group having 1 to 6 carbon atoms such as a methyl group and an ethyl group, a substituted or unsubstituted phenyl group, a hydroxyl group,

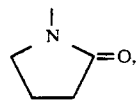

—CO—R and —O—R',
wherein
R is selected from the group consisting of a substituted or unsubstituted alkyl group having 1 to 10 carbon atoms such as a methyl group, an ethyl group and a propyl group, and —$(CH_2)_{n1}$—$X_{n2}$—$(CH_2)_{n3}$—$Y_{n4}$—$(CH_2)_{n5}$—CO—$R^7$,
wherein
X and Y each independently selected from the group consisting of —O— and —NH—,
$R^7$ is selected from the group consisting of —$NH_2$, —NH—$NH_2$ and —A—$R^8$,
wherein
A is selected from the group consisting of —O— and —S—, and
$R^8$ is selected from the group consisting of a substituted or unsubstituted alkyl group having 1 to 10 carbon atoms, a substituted or unsubstituted phenyl group and a substituted or unsubstituted succinimido group,
n1, n3 and n5 each independently represent an integer of 0 to 6, and
n2 and n4 each independently represent an integer of 0 or 1, and
R' has the same meaning as R, and
$R^2$ represents —$(CH_2)_{n1'}$—$X'_{n2'}$—$(CH_2)_{n3'}$—$Y'_{n4'}$—$(CH_2)_{n5'}$—CO—$R^{7'}$
wherein
X', Y', $R^{7'}$, n1', n2', n3', n4' and n5' respectively have the same meaning as X, Y, $R^7$, N1, n2, n3, n4 and n5.

In the formula [II]

[II]

$R^3$ is selected from the group consisting of a hydrogen atom, a substituted or unsubstituted alkyl group having 1 to 6 carbon atoms such as a methyl group and an ethyl group, a substituted or unsubstituted phenyl group, a hydroxyl group,

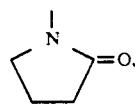

—CO—R and —O—R'
wherein
R and R' are as defined above, and
$R^4$ represents —$(CH_2)_{n1''}$—$X''_{n2''}$—$(CH_2)_{n3''}$—$Y''_{n4''}$—$(CH_2)_{n5''}$—CO—$R^9$
wherein
X", Y", n1",n2", n3", n4" and n5" respectively have the same meanings as X, Y, n1, n2, n3, n4 and n5, and
$R^9$ represents —A'—$R^{10}$,
wherein
A' has the same meaning as A, and
$R^{10}$ is selected from the group consisting of a hydrogen atom, an alkali metal, an alkaline earth metal, a substituted or unsubstituted alkyl group having 1 to 10 carbon atoms, a substituted or unsubstituted phenyl group and a substituted or unsubstituted succinimido group.

In the case where $R^7$ is —NH—$NH_2$, $R^{10}$ preferably represents a substituted or unsubstituted alkyl group having 1 to 10 carbon atoms or a substituted or unsubstituted phenyl group, and the —NH—$NH_2$ groups are unmodified, or part or all of the —NH—$NH_2$ groups are modified to form —$N_3$ groups.

In the formula [III]

[III]

$R^5$ is selected from the group consisting of a hydrogen atom, a substituted or unsubstituted alkyl group having 1 to 6 carbon atoms such as a methyl group and an ethyl group, a substituted or unsubstituted phenyl group, a hydroxyl group,

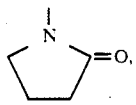

—CO—R and —O—R'
wherein
R and R' are as defined above, and
R⁶ is selected from the group consisting of a hydroxyl group,

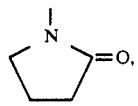

—CO—R and —O—R'
wherein
R and R' are as defined above.

Examples of substituents for the above-mentioned alkyl group having 1 to 6 or 1 to 10 carbon atoms include a halogen, an alkyl group having 1 to 6 carbon atoms, a hydroxyl group, a nitro group, a cyano group, a carboxyl group and a phenyl group. Examples of substituents for the above-mentioned phenyl group include a halogen, an alkyl group having 1 to 6 carbon atoms, a hydroxyl group, a nitro group, a carboxyl group and a phenyl group. Examples of substituents for the above-mentioned succinimido group include a halogen, an alkyl group having 1 to 6 carbon atoms, a hydroxyl group, a nitro group, a cyano group, a carboxyl group and a phenyl group.

In the present invention, where $R^1$ is a hydrogen atom, $R^2$ is —CO—NH₂ and the proportion of units (ii) is 0 mol percent, $R^6$ is selected from the group consisting of a hydroxyl group, —CO—R and —O—R'. Further, where $R^1$ is a hydrogen atom or a substituted or unsubstituted alkyl group having 1 to 6 carbon atoms, the proportions of units (i), (ii) and (iii) are respectively 1 to 95 mol percent, preferably 10 to 50 mol percent; 0 to 90 mol percent, preferably 0 to 50 mol percent; and 5 to 99 mol percent, preferably 30 to 90 mol percent, based on the total of units (i), (ii) and (iii).

The molecular weight of the protective polymer is preferably in the range of from 800 to 1,000,000, more preferably from 1,500 to 50,000. The molecular weight of the protective polymer can be determined by gel permeation chromatography (GPC).

Examples of the dispersion medium in the colloidal metal dispersion of the present invention include water, straight chain or branched alcohols each having 1 to 10 carbon atoms, water-miscible ethers such as dioxane, and mixtures thereof. Of them, preferred are water, methanol, ethanol and a mixture thereof. The amount of the dispersion medium is preferably in the range of from 10 to 5,000 mol, more preferably from 50 to 500 mol, per atom of the metal forming the colloidal particles.

The amount of the protective polymer is such that the total amount of the units (i), (ii) and (iii) is in the range of from 1 to 1,000 mol, preferably from 5 to 50 mol, per atom of the metal constituting the colloidal particles.

The polymer-protected colloidal metal of the present invention can be prepared, for example, by any of the following methods.

METHOD I

A metallic compound corresponding to a desired metal to be formed into colloidal particles is dissolved in a medium to prepare a solution containing metallic ions. As the metallic compound, there may be used those which dissolve in such a medium as mentioned below even in the presence of the above-mentioned protective polymer. Examples of the metallic compound include a halide, a nitrate, a sulfate, a carbonate, and a hydroxide. As the medium, there may generally be used water, a straight chain or branched alcohol having 1 to 10 carbon atoms, a water-miscible ether such as dioxane, and a mixture thereof. Preferably, there are used water, methanol, ethanol and mixtures thereof. The amount of the medium to be used is preferably in the range of from 10 to 5,000 mol, more preferably 50 to 500 mol per ion of the metal.

Next, a protective polymer comprising the units (i), (ii) and (iii) as mentioned before is added to the resulting solution containing metallic ions. The amount of the protective polymer to be added is such that the total amount of the units (i), (ii) and (iii) is in the range of from 1 to 1,000 mol, preferably from 5 to 50 mol, per ion of the metal. Thus, there is obtained a solution containing metallic ions and the protective polymer.

Then, the solution is subjected to reduction treatment to obtain a colloidal metal dispersion of the present invention. The method of the reduction treatment is not restricted, and may generally be performed by photoreduction or by means of a reducing agent.

In the case where photoreduction is employed, it may be carried out, for example, as follows. The solution containing metallic ions and the protective polymer is subjected to freeze-thaw treatment several times to degass the solution. The resulting degassed solution is irradiated with a high pressure mercury lamp, a low pressure mercury lamp, a tungsten lamp, an argon laser lamp, or the like.

In the case where a reducing agent is employed, the reduction may be carried out, for example, as follows. To the solution containing metallic ions and the protective polymer is added a reducing agent in an amount of 1 to 50 mol, preferably 1.5 to 10 mol per mol of the metallic compound used, followed by stirring at 10° to 100° C. for 1 minutes to 10 hours to obtain a colloidal metal dispersion of the present invention. Examples of the reducing agent include formaldehyde, hydrazine, sodium borohydride, an alcohol having 1 to 6 carbon atoms, etc. [see, for example, Shin Jikken Kagaku Koza 15 kan, Sanka to Kangen (II) (New Experimental Chemistry Vol. 15, Oxidation and Reduction (II)), pp 29–332(1977), Maruzen Co., Ltd., Japan]. Further, the reduction treatment may also be carried out by bubbling a hydrogen gas through the solution containing metallic ions and the protective polymer.

METHOD II

By the methods as will be described later, precursors of protective polymers (i.e., a precursor of protective polymer A which is one of the protective polymers as mentioned before wherein $R^7$ is —NH—NH₂; a precursor of protective polymer B which is another of the protective polymers as mentioned before wherein $R^7$ is —A—$R^8$; and a precursor of protective polymer C which is still another of the protective polymers as mentioned before wherein $R^7$ is —NH₂ are prepared. Using each of the precursors, substantially the same procedures as in Method I above are repeated except that the precursors are used in place of the corresponding protective polymers, to separately obtain preliminary colloidal metal dispersions in which colloidal particles of a metal are protected by the respective precursors of protective polymers A, B and C. The preliminary dispersions obtained are separately treated to obtain colloidal metal dispersions of the present invention.

That is, in the case of the preliminary dispersion in which the colloidal particles are protected by the precursor of the protective polymer A (i.e. the protective polymer wherein $R^7$ is —NH—NH$_2$), the preliminary dispersion is treated with hydrazine to convert the precursor to the protective polymer wherein $R^7$ is —NH—NH$_2$, thereby obtaining a colloidal metal dispersion of the present invention in which the colloidal particles are protected by the protective polymer having a hydrazide group (—CONHNH$_2$). The treatment with hydrazine may be carried out, for example, by adding to the preliminary dispersion 0.1 to 100 mol, per mol of the units (ii) in the precursor, of hydrazine, followed by stirring at a temperature in the range of from 10° C. to the boiling point of the medium, preferably from 30° to 80° C. for 30 minutes to 10 hours.

In the case of the preliminary dispersion in which the colloidal particles are protected by the precursor of the protective polymer B (i.e., the protective polymer wherein $R^7$ is —A—R$^8$), the preliminary dispersion is subjected to esterification or thioesterification to convert the precursor to the protective polymer wherein $R^7$ is —A—R$^8$, thereby obtaining a colloidal metal dispersion of the present invention in which the colloidal particles are protected by the protective polymer having an ester group or a thioester group. The manner of esterification or thioesterification is not specifically limited, and the treatment may be conducted according to the known methods described in "Shin Jikken Kagaku Koza 14 kan, Yuki Kagobutsu no Gosei to Hanno (II)" [New Experimental Chemistry, Vol. 14, Synthesis of Organic Compounds and Their Reaction (II)], pp 1000–1062(1977), Maruzen Co., Ltd., Japan. For example, the preliminary dispersion is refluxed using an acid as catalyst in the presence of an alcohol or a thioalcohol, followed by the removal of the water formed. Alternatively, the preliminary dispersion may be reacted with thionyl chloride and then with an alcohol or a thioalcohol.

In the case of the preliminary dispersion in which the colloidal particles are protected by the precursor of the protective polymer C (i.e., the protective polymer wherein $R^7$ is —NH$_2$), the preliminary dispersion is treated with ammonia to convert the precursor to the protective polymer wherein $R^7$ is —NH$_2$, thereby obtaining a colloidal metal dispersion of the present invention in which the colloidal particles are protected by the protective polymer having an amido group (CONH$_2$). The treatment with ammonia may be conducted according to the known methods described in "Shin Jikken kagaku Koza 14 kan, Yuki Kagobutsu no Gosei to Hanno (II)" [New Experimental Chemistry, Vol. 14, Synthesis of Organic Compounds and Their Reaction (II)], pp 1134–1189(1977), Maruzen Co., Ltd., Japan. For example, the treatment may be effected by adding to the preliminary dispersion 0.1 to 100 mol, per mol of the units (ii) in the precursor, of ammonia, followed by stirring at a temperature in the range of from 0° C. to the boiling point of the medium, preferably from 10° to 80° C. for 30 minutes to 10 hours. The ammonia may be added in the form of an aqueous solution or by bubbling gaseous ammonia through the preliminary dispersion.

METHOD III

In substantially the same manner as in Method I described above, a solution containing metallic ions is prepared. The solution thus obtained is then subjected to reduction treatment in substantially the same manner as in Method I to obtain a preliminary colloidal metal dispersion in which the colloidal particles have not yet been protected by a polymer. To the preliminary dispersion is added a protective polymer comprising the units (i), (ii) and (iii) as mentioned hereinbefore. The amount of the protective polymer to be added is such that the total amount of the units (i), (ii) and (iii) is in the range of from 1 to 1,000 mol, preferably from 5 to 50 mol, per atom of the metal constituting the colloidal particles.

The protective polymer comprising units (i), (ii) and (iii) as defined above may be prepared by customary methods. Examples of the preparation method are given below.

THE PROTECTIVE POLYMER WHEREIN $R^7$ IS —NH—NH$_2$ (Protective polymer A)

Monomer (iv) represented by the formula [IV] as defined below is polymerized with monomer (v) represented by the formula [V] as defined below to obtain a precursor of the protective polymer, and the precursor is then reacted with hydrazide to obtain the protective polymer having a hydrazide group (—CONHNH$_2$), i.e. the protective polymer wherein $R^7$ is —NH—NH$_2$ (protective polymer A). The proportions of monomers (iv) and (v) to be used are respectively 1 to 100 mol percent and 0 to 99 mol percent, based on the total amount of monomers (iv) and (v). The polymerization may be carried out by radical polymerization using a radical initiator, photo polymerization, irradiation polymerization, cationic polymerization and the like as explained later.

$$\begin{array}{cc} H & Z^1 \\ | & | \\ C=C \\ | & | \\ H & Z^2 \end{array} \qquad [IV]$$

wherein $Z^1$ is selected from the group consisting of a hydrogen atom, a substituted or unsubstituted alkyl group having 1 to 6 carbon atoms, a substituted or unsubstituted phenyl group, a hydroxyl group

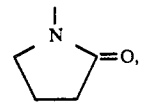

—CO—$Z^{1'}$ and —O—$Z^{1''}$, wherein $Z^{1'}$ is selected from the group consisting of a substituted or unsubstituted alkyl group having 1 to 10 carbon atoms such as a methyl group, an ethyl group and a propyl group and —(CH$_2$)$_{m1}$—X$^1_{m2}$—(CH$_2$)$_{m3}$—Y$^1_{m4}$—(CH$_2$)$_{m5}$—CO—NH—NH$_2$, wherein $X^1$ and $Y^1$ are each independently selected from the group consisting of —O— and —NH—, m1, m3 and m5 each independently represent an integer of 0 to 6, and m2 and m4 each independently represent an integer of 0 or 1, and $Z^{1''}$ is selected from the group consisting of a substituted or unsubstituted alkyl group having 1 to 10 carbon atoms such as a methyl group, an ethyl group and a propyl group and $-(CH_2)_{m1'}-X^{1'}_{m2'}-(CH_2)_{m3'}-Y^{1'}_{m4'}-(CH_2)_{m5'}-CO-\alpha'$ wherein $X^{1'}$ and $Y^{1'}$ are each independently selected from the group consisting of —O— and —NH—, $\alpha'$ is selected from the group consisting of —NH$_2$ and —$\gamma'$—$\beta'$ wherein $\gamma'$ is selected from the group consisting of —O— and —S—, and $\beta'$ is selected from the group consisting of a hydrogen atom, an alkali metal, an alkaline earth metal, a substituted or unsubstituted alkyl group having 1 to 10 carbon atoms, a substituted or unsubstituted phenyl group and a substituted or unsubstituted succinimido group, preferably selected from the group consisting of a substituted or unsubstituted alkyl group having 1 to 10 carbon atoms and a substituted or unsubstituted phenyl group, m1', m3' and m5' each independently represent an integer of 0 to 6, and m2' and m4' each independently represent an integer of 0 or 1, and $Z^2$ represents $-(CH_2)_{m1''}-X^{1''}_{m2''}-(CH_2)_{m3''}-Y^{1''}_{m4''}-(CH_2)_{m5''}-CO-\alpha$ wherein $X^{1''}$ and $Y^{1''}$ are each independently selected from the group consisting of —O— and —NH—, $\alpha$ is selected from the group consisting of —NH$_2$ and —$\gamma$—$\beta$ wherein $\gamma$ is selected from the group consisting of —O— and —S—, and $\beta$ is selected from the group consisting of a hydrogen atom, an alkali metal, an alkaline earth metal, a substituted or unsubstituted alkyl group having 1 to 10 carbon atoms, a substituted or unsubstituted phenyl group and a substituted or unsubstituted succinimido group, preferably selected from the group consisting of a substituted or unsubstituted alkyl group having 1 to 10 carbon atoms, an unsubstituted phenyl group and a phenyl group substituted with a nitro group or an alkyl group, m1'', m3'' and m5'' each independently represent an integer of 0 to 6, and m2'' and m4'' each independently represent an integer of 0 or 1.

$$\begin{array}{cc} H & Z^3 \\ | & | \\ C=C \\ | & | \\ H & Z^4 \end{array} \quad [V]$$

wherein $Z^3$ is selected from the group consisting of a hydrogen atom and a substituted or unsubstituted alkyl group having 1 to 6 carbon atoms such as a methyl group and an ethyl group, and $Z^4$ is selected from the group consisting of a hydroxyl group,

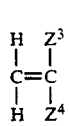

—CO—$Z^{1'}$ and —O—$Z^{1'''}$, wherein $Z^{1'}$ and $Z^{1'''}$ are as defined above.

As suitable substituents for the alkyl group having 1 to 6 or 1 to 10 carbon atoms, the phenyl group and the succinimido group, there may be mentioned those as given hereinbefore.

Examples of the monomer compound (iv) represented by the formula [IV] include acrylamide, methacrylamide, N,N-dimethylacrylamide, and a substituted or unsubstituted acrylate and methacrylate such as methyl acrylate, methyl methacrylate, ethyl acrylate, ethyl methacylate, phenyl acrylate, phenyl methacrylate, p-nitrophenyl acrylate, p-nitrophenyl methacrylate, trifluoroethyl acrylate and trifluoroethyl methacrylate, thiophenyl ester of acrylic acid, 4-nitrothiophenyl ester of methacrylic acid, succinimido ester of acrylic acid and succinimido ester of methacrylic acid.

Examples of the monomer compound (v) represented by the formula [V] include N-vinylpyrrolidone, a substituted N-vinylpyrrolidone, vinyl alcohol, methyl vinyl ether, ethyl vinyl ether and methyl vinyl ketone.

The polymerization of the monomer [IV] with the monomer [V] may be carried out according to the known methods described in "Shin Jikken kagaku Koza 19 kan, Kobunshi Kagaku (I)" [New Experimental Chemistry, Vol. 19, Polymer Chemistry (I)], pp 46-48(1978), Maruzen Co., Ltd., Japan. For example, the polymerization may be carried out by radical polymerization using, as radical initiator, benzoyl peroxide, azobisisobutyronitrile, potassium peroxodisulfate, etc, photo polymerization, irradiation polymerization, cationic polymerization and the like.

When a protective polymer having the units (i) and (ii) or a protective polymer having the units (i), (ii) and (iii) is desired, the ratio of the amount of the monomer [IV] to be used to the amount of the monomer [V] to be used may vary depending on the kind of the monomers, but generally be 0.1:100.

By the polymerization as described above, a precursor of the protective polymer is obtained. Then, the precursor is reacted with hydrazine to obtain a protective polymer having a hydrazide group (—CO—NHNH$_2$). For example, the reaction of the precursor with hydrazine may be conducted as follows. The precursor is dissolved in a medium, for example water, a straight chain or branched alcohol having 1 to 10 carbon atoms, a water-miscible ether such as dioxane, and a mixture thereof. Then, to the solution is added hydrazine in an amount of 0.1 to 100 mol per mol of the unit (ii) of formula [II] of the precursor, and the mixture is kept at a temperature in the range of from 10° C. to the boiling point of the medium, preferably from 30° to 80° C., for 30 minutes to 10 hours to obtain the protective polymer.

In the case where the precursor is a homopolymer of the monomer [IV], when all of the $\alpha$ groups, which $\alpha$ is as defined above, in the precursor are converted into —NH—NH$_2$ groups by the reaction with hydrazine, there is obtained a protective polymer consisting of the units (i). When the $\alpha$ groups in the precursor are partly converted into —NH—NH₂ groups, there is obtained a protective polymer consisting of the units (i) and (ii).

In the case where the precursor is a copolymer of the monomer [IV] and the monomer [V], when all of the α groups in the precursor are converted into —NH—NH₂ groups by the reaction with hydrazine, there is obtained a protective polymer consisting of the units (i) and (iii). When part of the α groups in the precursor is converted into —NH—NH₂ groups, there is obtained a protective polymer consisting of the units (i), (ii) and (iii).

THE PROTECTIVE POLYMER WHEREIN $R^7$ is —A—$R^8$ (Protective polymer B)

The protective polymer having an ester group or a thioester group, i.e. the protective polymer wherein $R^7$ is —A—$R^8$, may be obtained by known methods as follows. For example, 1 to 100 mol percent, based on the total amount of the monomers, of monomer [VI] represented by the formula [VI] as defined below is polymerized with 0 to 99 mol percent, based on the total amount of the monomers, of monomer [VII] represented by the formula [VII] as defined below by radical polymerization, photo polymerization, irradiation polymerization, cationic polymerization or the like to obtain a desired protective polymer. Alternatively, the protective polymer may be obtained by polymerizing 1 to 100 mol percent, based on the total amount of the monomers, of monomer [VIII] represented by the formula [VIII] as defined below with 0 to 99 mol percent, based on the total monomers, of monomer [VII] by radical polymerization, photo polymerization, irradiation polymerization, cationic polymerization or the like to obtain a precursor of the protective polymer, and then reacting the precursor with an alcohol or a thioalcohol to obtain a desired protective polymer.

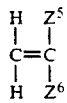   [VI]

wherein $Z^5$ and $Z^6$ respectively have the same meanings as $R^1$ and $R^2$.

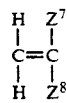   [VII]

wherein $Z^7$ and $Z^8$ respectively have the same meanings as $R^5$ and $R^6$.

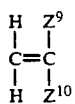   [VIII]

wherein $Z^9$ and $Z^{10}$ respectively have the same meaning as $R^3$ and $R^4$.

Examples of the monomer compound [VI] include substituted or unsubstituted acrylates and methacrylates such as methyl acrylate, methyl methacrylate, ethyl acrylate, ethyl methacrylate, phenyl acrylate, phenyl methacrylate, p-nitrophenyl acrylate, p-nitrophenyl methacrylate, trifluoroethyl acrylate and trifluoroethyl methacrylate, thiophenyl ester of acrylic acid, 4-nitrothiophenyl ester of methacrylic acid, succinimido ester of acrylic acid and succinimido ester of methacrylic acid.

Examples of the monomer compound [VII] include N-vinylpyrrolidone, a substituted N-vinylpyrrolidone, vinyl alcohol, methyl vinyl ether, ethyl vinyl ether and methyl vinyl ketone.

Examples of the monomer compound [VIII] include acrylic acid, methacrylic acid, an alkali metal salt and an alkaline earth metal salt of acrylic acid, and an alkali metal salt and an alkaline earth metal salt of methacrylic acid.

The polymerization of the monomer [VI] with the monomer [VII] and polymerization of the monomer [VIII] with monomer [VII] may be carried out according to the known methods described in "Shin Jikken Kagaku Koza 19 kan, Kobunshi Kagaku (I)" [New Experimental Chemistry, Vol. 19, Polymer Chemistry (I)], pp 46–48(1978), Maruzen Co., Ltd., Japan. For example, the polymerization may be carried out by radical polymerization using, as radical initiator, benzoyl peroxide, azobisisobutyronitrile, potassium peroxodisulfate, etc, photo polymerization, irradiation polymerization, cationic polymerization and the like. The ratio of the amount of the monomer [VI] or [VIII] to be used to the amount of the monomer [VII] to be used may vary depending on the kind of the monomers, but generally be 0.1:100.

In the case where monomer [VIII] and monomer [VII] is copolymerized to obtain a precursor of the protective polymer, the method of the subsequent esterification or thioesterification of the precursor is not specifically limited. For example, the esterification or thioesterification may be carried out by the known methods described in "Shin Jikken Kagaku Koza 14 kan, Yukikagobutsu no Gosei to Hanno (II)" [New Experimental Chemistry, Vol. 14, Synthesis of Organic Compound and Their Reaction (II)], pp 1000–1062(1977), Maruzen Co., Ltd., Japan. Illustratively stated, for example, the precursor is refluxed using an acid as catalyst in the presence of an alcohol or a thioalcohol, followed by the removal of the water formed. Alternatively, the precursor may be reacted with thionyl chloride and then with an alcohol or a thioalcohol. Examples of preferred alcohols include methanol, ethanol, propyl alcohol, butanol, phenol, cresol, 4-nitrophenol and 2,2,2-trifluoroethanol. Examples of preferred thioalcohols include thiophenol, 4-nitrothiophenol and thiobutanol and the like.

In the case where the precursor is a homopolymer of the monomer [VIII], when all of the carboxyl groups in the precursor are esterified or thioesterified, there is obtained a protective polymer consisting of the units (i). When the carboxyl groups in the precursor are partly esterified or thioesterified, there is obtained a protective polymer consisting of the units (i) and (ii).

In the case where the precursor is a copolymer of the monomer [VIII] and the monomer [VII], when all of the carboxyl groups in the precursor are esterified or thioesterified, there is obtained a protective polymer consisting of the units (i) and (iii). When the carboxyl groups in the precursor are partly esterified or thioesterified, there is obtained a protective polymer consisting of the units (i), (ii) and (iii).

THE PROTECTIVE POLYMER WHEREIN $R^7$ IS $-NH_2$, (Protective polymer C)

The protective polymer having an amido group ($-CONH_2$), i.e. the protective polymer wherein $R^7$ is $-NH_2$, may be obtained by known methods as follows. For example, 1 to 100 mol percent, based on the total amount of the monomers, of monomer [IX] represented by the formula [IX] as defined below is polymerized with 0 to 99 mol percent, based on the total amount of the monomers, of monomer [X] represented by the formula [X] as defined below by radical polymerization, photo polymerization, irradiation polymerization, cationic polymerization or the like to obtain the protective polymer. Alternatively, the protective polymer may be obtained by polymerizing 1 to 100 mol percent, based on the total amount of the monomers, of monomer [XI] represented by the formula [XI] as defined below with 0 to 99 mol percent, based on the total monomers, of monomer [X] by radical polymerization, photo polymerization, irradiation polymerization, cationic polymerization or the like to obtain a precursor of the protective polymer, and then reacting the precursor with ammonia to obtain the protective polymer.

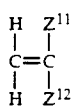     [IX]

wherein $Z^{11}$ and $Z^{12}$ respectively have the same meanings as $R^1$ and $R^2$.

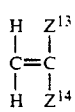     [X]

wherein $Z^{13}$ and $Z^{14}$ respectively have the same meanings as $R^5$ and $R^6$.

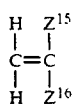     [XI]

wherein $Z^{15}$ and $Z^{16}$ respectively have the same meanings as $R^3$ and $R^4$.

Examples of the monomer compound [IX] include acrylamide, methacylamide, N,N-dimethylacrylamide and the like.

Examples of the monomer compound [X] include N-vinylpyrrolidone, a substituted N-vinylpyrrolidone, vinyl alcohol, methyl vinyl ether, ethyl vinyl ether and methyl vinyl ketone.

Examples of the monomer compound [XI] include acrylic acid, methacrylic acid, an alkali metal salt and an alkali earth metal salt of acrylic acid, an alkali metal salt and an alkaline earth metal salt of methacrylic acid, substituted or unsubstituted acrylates and methacrylates such as methyl acrylate, methyl methacrylate, ethyl acrylate, ethyl methacrylate, phenyl acrylate, phenyl methacrylate, p-nitrophenyl acrylate, p-nitrophenyl methacrylate, trifluoroethyl acrylate and trifluoroethyl methacrylate, thiophenyl ester of acrylic acid, thiophenyl ester of methacrylic acid, succinimido ester of acrylic acid and succinimido ester of methacrylic acid.

The polymerization of the monomer [IX] with the monomer [X] and the polymerization of the monomer [XI] with monomer [X] may be carried out according to the known methods described in "Shin Jikken Kagaku Koza 19 kan, Kobunshi Kagaku (I)" [New Experimental Chemistry, Vol. 19, Polymer Chemistry (I)], pp 46–48(1978), Maruzen Co., Ltd., Japan. For example, the polymerization may be carried out by radical polymerization using, as radical initiator, benzoyl peroxide, azobisisobutyronitrile, potassium peroxodisulfate, etc, photo polymerization irradiation polymerization, cationic polymerization and the like. The ratio of the amount of the monomer [IX] or [XI] to be used to the amount of the monomer [X] to be used may vary depending on the kind of the monomers, but generally be 0.1:100.

In the case where monomer [XI] and monomer [X] is copolymerized to obtain a precursor of the protective polymer, the method of the subsequent treatment of the precursor with ammonia is not specifically limited. Illustratively stated, for example, the precursor is dissolved in a medium, for example water, a straight chain or branched alcohol having 1 to 10 carbon atoms, a water-miscible ether such as dioxane, and a mixture thereof. Then, to the solution is added 0.1 to 100 mol, per mol of the units (ii) in the precursor, of ammonia, followed by stirring at a temperature in the range of from 0° C. to the boiling point of the medium, preferably from 10° to 80° C. for 30 minutes to 10 hours. The ammonia may be added in the form of an aqueous solution or by bubbling gaseous ammonia through the solution of the precursor. The ammonia treatment may be conducted under pressure.

In the above ammonia treatment, when all of the $-A'-R^{10}$ groups, wherein A' and $R^{10}$ are as defined hereinbefore, in the precursor are converted into $-NH_2$ groups by the reaction with ammonia, there is obtained a protective polymer consisting of the units (i) and (iii). When the $-A'-R^{10}$ groups in the precursor are partly converted into $-NH_2$ groups, there is obtained a protective polymer consisting of the units (i), (ii) and (iii).

The polymer-protected colloidal metal dispersion of the present invention is extremely stable for a long period of time. Further, the colloidal metal particles in the dispersion, which are protected by the specific protective polymer according to the present invention, are easily and strongly bound to various amino group-containing compounds to give stable colloidal metal complexes having a wide variety of uses, such as the use as a solid catalyst for various reactions, the use for the treatment and diagnosis of various diseases, the use for the study of tissues of living bodies, the use for inducing mutation of microorganisms, etc.

In another aspect of the present invention, there is provided a colloidal metal complex comprising:

colloidal particles of at least one metal selected from the group consisting of metals belonging to Groups Ib, VIIb and VIII of the Periodic Table;

an amino group-containing compound; and a protective polymer adsorbed on said colloidal particles, said protective polymer comprising 1 to 100 mol percent, based on the total of units (i), (ii) and (iii), of units (i) represented by the formula [I]

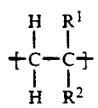  [I]

wherein

R$^1$ is selected from the group consisting of a hydrogen atom, a substituted or unsubstituted alkyl group having 1 to 6 carbon atoms, a substituted or unsubstituted phenyl group, a hydroxyl group,

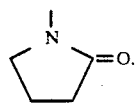

—CO—R and —O—R',
wherein

R is selected from the group consisting of a substituted or unsubstituted alkyl group having 1 to 10 carbon atoms and —(CH$_2$)$_{n1}$—X$_{n2}$—(CH$_2$)$_{n3}$—Y$_{n4}$—(CH$_2$)$_{n5}$—CO—R$^7$,
wherein X and Y are each independently selected from the group consisting of —O— and —NH—, R$^7$ is selected from the group consisting of —N-H—NH$_2$, —A—R$^8$ and —NH$_2$,
wherein A is selected from the group consisting of —O— and —S—, and R$^8$ is selected from the group consisting of a substituted or unsubstituted alkyl group having 1 to 10 carbon atoms, a substituted or unsubstituted phenyl group and a substituted or unsubstituted succinimido group, n1, n3 and n5 each independently represent an integer of 0 to 6, and n2 and n4 each independently represent an integer of 0 or 1, and R' has the same meaning as R, and R$^2$ represents —(CH$_2$)$_{n1'}$—X'$_{n2'}$—(CH$_2$)$_{n3'}$—Y'$_{n4'}$—(CH$_2$)$_{n5'}$—CO—R$^{7'}$
wherein X', Y', R$^{7'}$, n1', n2', n3', n4' and n5' respectively have the same meanings as X, Y, R$^7$, n1, n2, n3, n4 and n5;

0 to 99 mol percent, based on the total of units (i), (ii) and (iii), of units (ii) represented by the formula [II]

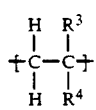  [II]

wherein

R$^3$ is selected from the group consisting of a hydrogen atom, a substituted or unsubstituted alkyl group having 1 to 6 carbon atoms, a substituted or unsubstituted phenyl group, a hydroxyl group,

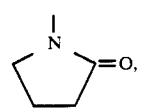

—CO—R and —O—R'
wherein

R and R' are as defined above, and

R$^4$ represents —(CH$_2$)$_{n1''}$—X''$_{n2''}$—(CH$_2$)$_{n3''}$—Y''$_{n4''}$—(CH$_2$)$_{n5''}$—CO—R$^9$
wherein X'', Y'', n1'', n2'', n3'', n4'' and n5'' respectively have the same meanings as X, Y, n1, n2, n3, n4 and n5, and R$^9$ represents —A'—R$^{10}$,
wherein A' has the same meaning as A, and R$^{10}$ is selected from the group consisting of a hydrogen atom, an alkali metal, an alkaline earth metal, a substituted or unsubstituted alkyl group having 1 to 10 carbon atoms, a substituted or unsubstituted phenyl group and a substituted or unsubstituted succinimido group; and 0 to 99 mol percent, based on the total of units (i), (ii) and (iii), of units (iii) represented by the formula [III]

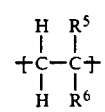  [III]

wherein

R$^5$ is selected from the group consisting of a hydrogen atom, a substituted or unsubstituted alkyl group having 1 to 6 carbon atoms, a substituted or unsubstituted phenyl group, a hydroxyl group,

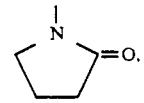

—CO—R and —O—R'
wherein

R and R' are as defined above, and

R$^6$ is selected from the group consisting of a hydroxyl group

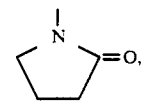

—CO—R and —O—R'
wherein

R and R' are as defined above;

said protective polymer being bonded to said amino group-containing compound directly or through the residue of a bifunctional compound reactive to an amino group, thereby binding said colloidal particles to said amino group-containing compound;

provided that where R$^1$ is a hydrogen atom or a substituted or unsubstituted alkyl group having 1 to 6 carbon atoms, the proportions of units (i), (ii) and (iii) are respectively 1 to 95 mol percent, 0 to 90 mol percent and 5 to 99 mol percent, based on the total of units (i), (ii) and (iii);

where

R$^7$ is —NH—NH$_2$, the —NH—NH$_2$ groups are unmodified, or part or all of the —NH—NH$_2$ groups are modified to form —N$_3$ groups;

where $R^7$ is —A—$R^8$, said colloidal particles are bound to said amino group-containing compound directly; and where said protective polymer is a copolymer of acrylamide and N-vinyl-2-pyrrolidone and said amino group-containing compound is aminoethylated polyacrylamide, said protective polymer is bonded to said amino group-containing compound through the residue of a bifunctional compound reactive to an amino group.

In the colloidal metal complex of the present invention, in the case where the protective polymer has an ester group or an thioester group, i.e., $R^7$ of the protective polymer is —A—$R^8$, the colloidal metal particles protected by the protective polymer are bound to said amino group-containing compound directly. The protective polymer adsorbed on the colloidal metal particles is chemically bonded to an amino group-containing compound directly, thereby binding the colloidal metal particles to the amino group-containing compound. In the case where the protective polymer has a hydrazide group (—CONHNH$_2$) or an amido group (—CONH$_2$), i.e., $R^7$ of the protective polymer is —NH— NH$_2$ or —NH$_2$, the protective polymer adsorbed on the colloidal metal particles is chemically bonded to an amino group-containing compound directly or through the residue of a bifunctional compound to an amino group, thereby binding the colloidal metal particles to the amino group-containing compound, provided that where the protective polymer is a copolymer of acrylamide and N-vinyl-2-pyrrolidone and the amino group-containing compound is aminoethylated polyacrylamide, it is bonded to an amino group-containing compound only through the residue of a bifunctional compound reactive to an amino group.

The colloidal metal particles bound to the amino group-containing compound are protected by the above-described protective polymers. The protective polymer comprises 1 to 100 mol percent, preferably 10 to 50 mol percent of units (i) represented by the above-defined formula [I], 0 to 99 mol percent, preferably 0 to 50 mol percent of units (ii) represented by the above-defined formula [II] and 0 to 99 mol percent, preferably 30 to 90 mol percent of units (iii) represented by the above-defined formula [III], based on the total of units (i), (ii) and (iii).

In the case where $R^7$ in the protective polymer is —NH—NH$_2$, the —NH—NH$_2$ groups may be unmodified, or part or all of the —NH—NH$_2$ groups may be modified to form —N$_3$ groups. Preferably, 30 mol percent or more of the —NH—NH$_2$ groups may be modified into —N$_3$ groups.

The bifunctional compound may be a compound having two functional groups selected from the group consisting of an aldehyde group, an isocyante group, a maleimide group, an iodoacetamide group and a diazobenzidine group. Examples of the bifunctional compound reactive to an amino group include dialdehydes represented by OHC—(CH$_2$)$_n$—CHO, wherein n is an integer of 0 to 7, such as glutaraldehyde; hexamethylenediisocyanate; N,N'-ethylenebismaleimide; N,N'-polymethylenebisiodoacetamide and bisdiazobenzidine, and the like.

The kind of the amino group-containing compound is not specifically limited, and any compound containing an amino group may be employed according to the use of the colloidal metal complex. Examples of the amino group-containing compound include a homopolymer or copolymer of a vinyl compound which has a primary and/or a secondary amino group, a nucleic acid and a protein. Representative examples of the above-mentioned homopolymer and copolymer include a crosslinked or uncrosslinked polyaminostyrene such as poly(4-aminostyrene) and a copolymer of 4-aminostyrene and styrene, a crosslinked or uncrosslinked polyallylamine, and an amino ($C_1$-$C_6$) alkylated polyacrylamide. Examples of the amino group-containing compound also include an amino group-containing nucleic acid such as DNA and RNA; a nucleic acid such as thymidylic acid into which an amino group is introduced; proteins such as isomerase, peroxidase, urease, ATPase, hormones including insulin, an antigen and an antibody; sugars, such as heparin, mucopolysaccharides and keratan sulfate, into which an amino group is introduced; lipids into which an amino group is introduced. In the case of a compound having no amino groups, an amino group is chemically introduced into the compound and the thus modified compound may be employed as an amino group-containing compound.

The metal constituting the colloidal particles bound to the amino group-containing compound is at least one selected from the group consisting of metals belonging to Groups Ib, VIIb and VIII of the Periodic Table, preferably selected from the group consisting of gold, silver, platinum, ruthenium, rhodium, palladium, osmium, rhenium, iridium, copper and nickel. The metal may be radioactive one, such as radioactive gold, radioactive silver and radioactive platinum. The colloidal particles of the metal is protected by the above-described specific protective polymer as explained hereinbefore, and generally have a diameter of from 5 to 1000 Å.

In the colloidal metal complex of the present invention, the proportion of the amino group-containing compound is not critical. However, the amount of the amino group-containing compound may be generally in the range of 0.01 to 1 mol, preferably 0.1 to 1 mol or more per mol of the hydrazide group, azido group, ester group, thioester group and amido group contained in the protective polymer.

The colloidal metal complex of the present invention may be analyzed qualitatively and quantitatively as follows. The kind and amount of the colloidal metal may be determined by dissolving the colloidal metal complex in aqua regia or the like and subjecting the resultant solution to atomic absorption analysis. The composition of the protective polymer may be determined by subjecting the colloidal metal complex to infrared absorption analysis, NMR analysis, elementary analysis and the like.

In a further aspect of the present invention, there is provided a method for the preparation of a colloidal metal complex comprising:

colloidal particles of at least one metal selected from the group consisting of metals belonging to Groups Ib, VIIb and VIII of the Periodic Table;

an amino group-containing compound; and a protective polymer adsorbed on said colloidal particles, said protective polymer being bonded to said amino group-containing compound directly, thereby binding said colloidal particles to said amino group-containing compound;

said protective polymer comprising 1 to 100 mol percent, based on the total of units (i), (ii) and (iii), of units (i) represented by the formula [I]

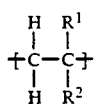
[I]

wherein

R¹ is selected from the group consisting of a hydrogen atom, a substituted or unsubstituted alkyl group having 1 to 6 carbon atoms, a substituted or unsubstituted phenyl group, a hydroxyl group,

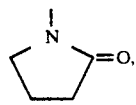

—CO—R and —O—R',
wherein

R is selected from the group consisting of a substituted or unsubstituted alkyl group having 1 to 10 carbon atoms and —$(CH_2)_{n1}$—$X_{n2}$—$(CH_2)_{n3}$—$Y_{n4}$—$(CH_2)_{n5}$—CO—$R^7$,
wherein X and Y are each independently selected from the group consisting of —O— and —NH—, $R^7$ is selected from the group consisting of —NH—NH₂, —A—$R^8$ and —NH₂,
wherein A is selected from the group consisting of —O— and —S13, and $R^8$ is selected from the group consisting of a substituted or unsubstituted alkyl group having 1 to 10 carbon atoms, a substituted or unsubstituted phenyl group and a substituted or unsubstituted succinimido group, n1, n3 and n5 each independently represent an integer of 0 to 6, and n2 and n4 each independently represent an integer of 0 or 1, and R' has the same meaning as R, and $R^2$ represents —$(CH_2)_{n1'}$—$X'_{n2'}$—$(CH_2)_{n3'}$—$Y'_{n4'}$—$(CH_2)_{n5'}$—CO—$R^{7'}$
wherein X', Y', $R^{7'}$, n1', n2', n3', n4' and n5' respectively have the same meanings as X, Y, $R^7$, n1, n2, n3, n4 and n5;

0 to 99 mol percent, based on the total of units (i), (ii) and (iii), of units (ii) represented by the formula [II]

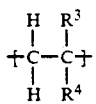
[II]

wherein $R^3$ is selected from the group consisting of a hydrogen atom, a substituted or unsubstituted alkyl group having 1 to 6 carbon atoms, a substituted or unsubstituted phenyl group, a hydroxyl group,

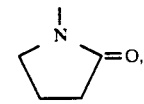

—CO—R and —O—R'
wherein

R and R' are as defined above, and $R^4$ represents —$(CH_2)_{n1''}$—$X''_{n2''}$—$(CH_2)_{n3''}$—$Y''_{n4''}$—$(CH_2)_{n5''}$—CO—$R^9$
wherein X'', Y'', n1'', n2'', n3'', n4'' and n5'' respectively have the same meanings as X, Y, n1, n2, n3, n4 and n5, and $R^9$ represents —A'—$R^{10}$,
wherein A' has the same meaning as A, and $R^{10}$ is selected from the group consisting of a hydrogen atom, an alkali metal, an alkaline earth metal, a substituted or unsubstituted alkyl group having 1 to 10 carbon atoms, a substituted or unsubstituted phenyl group and a substituted or unsubstituted succinimido group; and 0 to 99 mol percent, based on the total of units (i), (ii) and (iii), of units (iii) represented by the formula [iii]

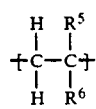
[III]

wherein $R^5$ is selected from the group consisting of a hydrogen atom, a substituted or unsubstituted alkyl group having 1 to 6 carbon atoms, a substituted or unsubstituted phenyl group, a hydroxyl group,

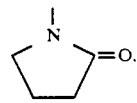

—CO—R and —O—R'
wherein

R and R' are as defined above, and $R^6$ is selected from the group consisting of a hydroxyl group,

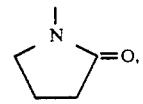

—CO—R and —O—R'
wherein

R and R' are as defined above;

which comprises contacting an amino group-containing compound with a polymer-protected colloidal metal dispersion comprising (a) a dispersion medium;

(b) colloidal particles of at least one metal selected from the group consisting of metals belonging to Groups Ib, VIIb and VIII of the Periodic Table, said colloidal particles being dispersed in said dispersion medium; and (c) a protective polymer adsorbed on said colloidal particles, said protective polymer being as defined above, provided that where R¹ is a hydrogen atom or a substituted or unsubstituted alkyl group having 1 to 6 carbon atoms, the proportions of units (i), (ii) and (iii) are respectively 1 to 95 mol percent, 0 to 90 mol percent and 5 to 99 mol percent, based on the total of units (i), (ii) and (iii), and where said protective polymer is a copolymer of acrylamide and N-vinyl-2-pyrrolidone, said amino group-containing compound is exclusive of aminoethylated polyacrylamide.

The colloidal metal particles can be bound to an amino group-containing compound by contacting the amino group-containing compound with the polymer-protected colloidal metal dispersion as described hereinbefore to react the amino groups in the amino group-containing compound with the protective polymer adsorbed on the colloidal metal particles, thereby forming a chemical linkage between the amino group-containing compound and the protective polymer. The contact of the amino group-containing compound with the polymer-protected colloidal metal dispersion may be effected, for example in an appropriate medium while stirring, for generally 10 minutes to 30 hours, preferably 30 minutes to 10 hours.

The amino group-containing compound to be used is not specifically limited, and may be selected according to the use of the colloidal metal complex to be prepared. Examples of suitable amino group-containing compounds are given hereinbefore. The amount of the amino group-containing compound to be used may be 0.1 to 100 mol, preferably 1 to 10 mol per mol of hydrazide group, ester group, thioester group and amido group in the protective polymer adsorbed on the colloidal metal particles.

As a suitable medium to be employed for the contact of the amino group-containing compound with the polymer-protected colloidal metal dispersion, there may be mentioned, for example, water, a straight chain or branched alcohol having 1 to 6 carbon atoms, and combinations thereof. Preferably, water, methanol, ethanol and combinations thereof are employed. The amount of the medium may generally be 10 to 1000 mol, preferably 50 to 300 mol per mol of the amino groups in the amino group-containing compound.

The temperature for the contact of the amino group-containing compound with the colloidal metal dispersion may generally be $-20°$ to $100°$ C. However, when natural polymers such as a protein are employed as the amino group-containing compound, the temperature is preferably $-10°$ to $20°$ C. for the purpose of preventing the natural polymers from denaturation. The pH of the medium is not critical, and may be generally 4 to 10.

In a further aspect of the method of the present invention, when a colloidal metal dispersion in which the colloidal metal particles are protected by the protective polymer wherein $R^7$ is $-NH-NH_2$ or $-NH_2$ is employed to be contacted with an amino group-containing compound, the polymer-protected colloidal metal dispersion is reacted, before contacted with an amino group-containing compound, with a bifunctional compound reactive to an amino group to obtain a reaction product. Subsequently, the reaction product is contacted with an amino group-containing compound to obtain a colloidal metal complex in which the colloidal metal particles are bound to the amino group-containing compound through the residue of the bifunctional compound reactive to an amino group.

Examples of the bifunctional compound reactive to an amino group are shown hereinbefore.

By the above-mentioned treatment with the bifunctional compound, the reactivity of the polymer-protected colloidal metal with an amino group-containing compound can be increased and, hence, the binding of the polymer-protected colloidal metal to an amino group-containing compound can be performed more easily.

The reaction of the polymer-protected colloidal metal dispersion with the bifunctional compound may be conducted by contacting the colloidal metal dispersion with the bifunctional compound in a medium, such as water, a straight chain or branched alcohol having 1 to 6 carbon atoms, or a combination thereof, while stirring at $5°$ to $60°$ C. for 1 to 20 hours. The amount of the bifunctional compound may be 1 to 50 mol, preferably 1.5 to 20 mol per mol of the hydrazide group and amido group in the protective polymer. The amount of the medium may generally be 5 to 200 mol per mol of the bifunctional compound used.

Then, the reaction product obtained is contacted with an amino group-containing compound after isolating the reaction product from the reaction mixture or without isolating the reaction product, to obtain a colloidal metal complex in which the colloidal metal particles are bound to the amino group-containing compound through the residue of the bifunctional compound. The contact of the reaction product with the amino group-containing compound may be effected under substantially the same conditions as those for the above-described contact of the polymer-protected colloidal metal dispersion with an amino group-containing compound.

Alternatively, the polymer-protected colloidal metal dispersion may be contacted with an amino group-containing compound in the presence of a bifunctional compound reactive to an amino group. The amount of the amino group-containing compound may be 0.1 to 100 mol, preferably 1 to 10 mol per mol of the hydrazide group and amido group in the protective polymer. The amount of the bifunctional compound may be 1 to 50 mol, preferably 1.5 to 20 mol per mol of the hydrazide group and amido group in the protective polymer.

The above contact of the colloidal metal dispersion with the amino group-containing compound may generally be effected in a medium at $0°$ to $100°$ C. for 1 to 20 hours while stirring. As the medium, there may be used, for example water, a straight chain or branched alcohol having 1 to 6 carbon atoms, and combinations thereof. Preferably, water, methanol, ethanol and combinations thereof are employed. The amount of the medium may generally be 10 to 1000 mol, preferably 50 to 300 mol per mol of the amino groups in the amino group-containing compound.

By the presence of the bifunctional compound during the contact, the reactivity of the polymer-protected colloidal metal dispersion can be increased and, hence, the polymer-protected colloidal metal can be bound to the amino group-containing compound more easily.

In an even further aspect of the method of the present invention, when a colloidal metal dispersion in which the colloidal metal particles are protected by the protective polymer wherein $R^7$ is $-NH-NH_2$ is employed to be contacted with an amino group-containing compound, the polymer-protected colloidal metal dispersion is reacted, before contacted with an amino group-containing compound, with nitrous acid or a nitrite such as sodium nitrite to convert part or all of the $-NH-NH_2$ groups in the protective polymer into $-N_3$ groups. Subsequently, the reaction product obtained is contacted with an amino group-containing compound to obtain a colloidal metal complex.

The reaction of the polymer-protected colloidal metal dispersion with nitrous acid or a nitrite may be conducted by contacting the colloidal metal dispersion with nitrous acid or a nitrite in a medium, such as water, a straight chain or branched alcohol having 1 to 6 carbon atoms, or a combination thereof, while stirring at 10° to 60° C. for 1 to 10 hours. The amount of nitrous acid or a nitrite may be 1 to 10 mol per mol of the hydrazide group in the protective polymer. The amount of the medium may generally be 5 to 200 mol per mol of nitrous acid or a nitrite used.

Then, the reaction product obtained is contacted with an amino group-containing compound, after isolating the reaction product from the reaction mixture or without isolating the reaction product, to obtain a colloidal metal complex. The contact of the reaction product with the amino group-containing compound may be effected under substantially the same conditions as those for the above-described contact of the polymer-protected colloidal metal dispersion with an amino group-containing compound.

Alternatively, the polymer-protected colloidal metal dispersion may be contacted with an amino group-containing compound in the presence of nitrous acid or a nitrite. The amount of nitrous acid or a nitrite used may be 1 to 10 mol per mol of the hydrazide group in the protective polymer. The amount of the amino group-containing compound may be 0.1 to 100 mol, preferably 1 to 10 mol per mol of the hydrazide group and azido group in the protective polymer.

The above contact of the colloidal metal dispersion with the amino group-containing compound may generally be effected in a medium at 0° to 100° C. for 1 to 20 hours while stirring. As the medium, there may be used, for example, water, a straight chain or branched alcohol having 1 to 6 carbon atoms, and combinations thereof. The amount of the medium may generally be 5 to 200 mol per mol of the nitrous acid or nitrite used.

By the above-mentioned treatment with nitrous acid or a nitrite or by the presence of nitrous acid or a nitrite, the reactivity of the polymer-protected colloidal metal dispersion can be increased and, hence, the polymer-protected colloidal metal can be bound to the amino group-containing compound more easily.

After or during the above-described processes for preparing the colloidal metal complex, that the polymer-protected colloidal metal particles have been bound to the amino group-containing compound may be confirmed as follows.

In the case where the amino group-containing compound is insoluble in the medium, as the colloidal metal particles are immobilized onto the amino group-containing compound, the color of the medium gradually becomes clear and the amino group-containing compound is colored. For example, a polymer-protected colloidal platinum dispersion in which the colloidal platinum particles are protected by a copolymer of acrylamide and N-vinyl-2-pyrrolidone is contacted with an amino group-containing compound, the black color of the medium due to the colloidal platinum becomes clear, and the amino group-containing compound becomes black. This color change may be utilized to confirm the immobilization. Further, after completion of the immobilizing procedure, the obtained colloidal metal complex is washed well with water or an alcohol, dissolved in aqua regia, and subjected to atomic absorption analysis to confirm the presence of the metal.

On the other hand, in the case where the amino group-containing compound is soluble in the medium, the colloidal metal particles are bound to the dissolved amino group-containing compound in situ. The obtained liquid containing the colloidal metal complex is subjected to gel permeation chromatography to obtain a chromatogram showing a peak at a position different from those for the peaks ascribed to the amino group-containing compound and the protective polymer, indicating that the polymer-protected colloidal particles are bound to the amino group-containing compound. Further, in the case where the amino group-containing compound is an enzyme, when the obtained liquid containing the colloidal metal complex is passed through a column packed with a gel capable of specifically adsorbing the enzyme, the enzyme, together with the colloidal metal, is adsorbed on the gel, indicating that the polymer-protected colloidal particles are bound to the amino group-containing compound, i.e. enzyme.

The thus obtained colloidal metal complex may be used as such, namely in the form of a solution or dispersion, for various purposes. Further, the colloidal metal complex may also be used in an isolated form after separating from the dispersion medium by means of various well-known filtration techniques, column chromatography, etc. depending upon the particle size of the colloidal metal complex.

The colloidal metal complex of the present invention may be advantageously used in a wide variety of applications. For example, a colloidal metal complex in which the polymer-protected colloidal metal particles are immobilized onto an ion exchange such as a cross-linked or uncrosslinked polyallylamine, crosslinked or uncrosslinked polyaminostyrene or other amino group-containing compounds insoluble in the solvent to be used for hydrogenation of olefins or dienes and hydration of nitriles is advantageously utilized as a solid catalyst effective for the hydrogenation of olefins or dienes, hydration of nitriles, etc. After used as catalyst, such a colloidal metal complex can be easily recovered from the reaction mixture by decantation, filtration, etc. and can be repeatedly used as catalyst.

Further, the colloidal metal complex in which the polymer-protected colloidal metal particles are bound to an enzyme, nucleic acid, antigen, antibody, etc. is useful for the study of tissues of a living body, the diagnosis and treatment of various diseases, the induction of mutation of microorganisms, etc. For example, there have conventionally been made studies on the structure of a tropomyosin-troponin complex which exists in a muscular tissue, by means of X-ray diffraction etc. However, it has been impossible to directly observe by an electron microscope how the troponin is bonded to the tropomyosin because the troponin is invisible by an electron microscope. However, when the polymer-protected colloidal metal particles of the present invention are bound to troponin, the troponin, becomes visible by an electron microscope because the colloidal metal particle bound to the troponin has such a sufficient size as is visible by an electron microscope. Therefore, when the tropomyosin-troponin complex is artificially prepared using troponin having colloidal particles bound thereto, and the resulting complex is observed by an electron microscope, the state of bonding between the troponin and the tropomyosin can be observed as will be explained in Example 2 given later.

Further, using as the colloidal metal a radioactive metal such as a radioactive gold, a radioactive platinum and a radioactive silver, the colloidal particles of the colloidal metal dispersion of the present invention may advantageously be bound to an antibody antigen. The resulting antigen is useful for the diagnosis and treatment of a cancer. Furthermore, the radioactive colloidal metal particles of the colloidal metal dispersion of the present invention may advantageously be bound to an oligomer of nucleic acids containing cytosine residues and/or adenine residues in the non-sense code region thereof (the region irrespective to genetic information), or an oligomer of nucleic acids, into which an amino group has been introduced by chemical modification at a portion of the non-sense code region. Such a complex of radioactive colloidal metal particle and oligomer of nucleic acids is useful in inducing mutation of strains of a bacterium such as *Escherichia coli* and a yeast to obtain mutant strains which are excellent in heat stability, acid resistance and alkali resistance as compared with the parent strains and which are capable of growing faster than the parent strains. That is, in the induction of mutation of a strain, the complex of radioactive colloidal metal particles and nucleic acids are transferred into cells of the above-mentioned strain, and the cells are cultured so that the cells are affected by a radiation emitted from the radioactive metal in the colloidal metal-oligomer complex. The resultant mutant strains can be advantageously used as a host in producing a polypeptide by means of recombinant DNA technique.

The present invention will now be described in more detail with reference to the following Examples that by no means limit the scope of the invention.

EXAMPLE 1

To 16 g of water are added 1.5 g of acrylamide, 22 g of N-vinyl-2-pyrrolidone and 0.05 g of benzoyl peroxide. The resulting mixture is heated at 80° C. for 12 hours while stirring to obtain a copolymer of acrylamide and N-vinyl-2-pyrrolidone. NMR spectrum analysis of the thus-obtained copolymer shows that the acrylamide content of the copolymer is 37% by mole.

2 g of the copolymer is dissolved in 50 ml of water, and heated over a hot bath at 50° C. for 45 minutes. To the resulting solution is added 9 g of hydrazine monohydrate, and reacted at 50° C. for 6 hours while stirring with a magnetic stirrer. The resulting solution is poured into 1000 g of 1,4-dioxane, thereby forming a white precipitate. The supernatant is removed by decantation, and the precipitate is dried in vacuo to obtain a purified copolymer of acrylamide and N-vinyl-2-pyrrolidone having a hydrazide group.

The hydrazide group content of this copolymer is determined according to the method described in Biochemistry, vol. 8, p. 4074,(1969), which is 0.38 milliequivalent per g of the copolymer. Further, the molecular weight of the hydrazide group-containing copolymer is determined by gel permeation chromatography in which use is made of G5000PW and G3000PW columns manufactured and sold by Toyo Soda Co., Ltd., Japan and water as a solvent. The molecular weight of the copolymer is about 28,000. Then, 0.11 g of the hydrazide group-containing copolymer is dissolved in 50 ml of a 1:1 by volume mixed solvent of ethanol and water, and to the resultant solution is added 5 ml of a $1.1 \times 10^{-2}$ mol/l aqueous solution of potassium tetrachloroplatinate. The mixture is subjected to freeze-thaw treatment twice to effect degassing, and then irradiated with the light from a 500 W high pressure mercury lamp for 2 hours while stirring with a magnetic stirrer to obtain a uniform blackish brown dispersion of colloidal platinum protected by the hydrazide group-containing copolymer. Measurement of the colloidal dispersion by the use of a transmission type electron microscope of model HU-12A manufactured and sold by Hitachi Ltd., Japan shows that the average particle diameter of the colloidal platinum particles is 30 Å, and that the colloidal platinum particles are uniformly dispersed in the dispersion. The colloidal dispersion is very stable. That is, even when the colloidal dispersion is centrifuged at 5000 rpm for 10 min, precipitation of colloidal platinum particles does not occur. Moreover, even when the colloidal dispersion is allowed to stand still at room temperature for a period of more than a month, any formation of colloidal platinum precipitates is not found.

EXAMPLE 2

To the dispersion of colloidal platinum protected by the hydrazide group-containing copolymer as obtained in Example 1 is added 5 g of a 14% by weight aqueous solution of glutaraldehyde. The resulting mixture having a pH value of 7.2 is heated at 32° C. for 12 hours. The resulting product is purified using Sephadex (trade mark) G-25 column manufactured and sold by Pharmacia Fine Chemicals, Sweden. To the resulting purified product is added 5 mg of troponin taken from a rabbit, and reacted at 4° C. for 12 hours thereby to bind the colloidal platinum particles protected by the hydrazide group-containing copolymer to the troponin. An aliquot of the resulting colloidal dispersion is subjected to gel permeation chromatography using G5000PW and G3000PW columns manufactured and sold by Toyo Soda Co., Ltd., Japan and water as a solvent. Thus, a chromatogram is obtained, which shows a peak at a position different from those for the peaks ascribed to the troponin and the copolymer present on the colloidal particles. This indicates that the copolymer-protected colloidal platinum particles is bound to the troponin. Then, fractions of the product composed of the troponin and, bound thereto, the copolymer-protected colloidal platinum particles are taken, and the fractions are subjected to amino acid analysis, thereby determining the amount of the troponin contained in the product. The amount of the troponin is 0.04 mol per mol of the structural unit having a glutaraldehyde group of the copolymer. Subsequently, to 20 g of the above-mentioned colloidal dispersion containing the product composed of the troponin and, bound thereto, the copolymer-protected colloidal platinum particles is added 50 mg of paracrystalline rabbit tropomyocin. The resulting mixture having a pH value of 7.5 is heated at 4° C. for 12 hours to obtain a complex of the tropomyocin and the product composed of the troponin and, bound thereto, the copolymer-protected colloidal platinum particles. The complex is stained with a 1% by weight aqueous solution of uranyl acetate, and examined by an electron microscope JEM 100-CX with a magnification of 307,500 manufactured and sold by Japan Electronic Machine Co., Ltd., Japan. A diagrammatic illustration of the electron photomicrograph is shown in the accompanying Figure. As is seen from the drawing, the platinum particles (2) are clearly observed on the tropomyosin paracrystal (1) with banding pattern. The platinum particles are bound to the troponin. Thus, the troponin binding cite in the paracrystal can be directly observed by the location of the platinum particles using an electron micrograph. The location of the platinum particles corresponds to the diad axes, i.e., the axes about which a rotation of 180° produces the same structure, of the paracrystal. This location is consistent with that reported for the location of the troponin binding cite on tropomyosin as reported by Stewart, *Proc. R. Soc. Lond. B.* 190,257(1975). The polymer-protected colloidal metal dispersion therefore is useful as a label for examining the binding state of different protein in body tissues.

EXAMPLE 3

A hydrazide group-containing copolymer is obtained in substantially the same manner as described in Example 1. 0.047 g of the copolymer is dissolved in 15 ml of a 1:1 by volume mixed solvent of ethanol and water, and 5 ml of a $4 \times 10^{-3}$ mol/l aqueous solution of potassium tetrachloroplatinate is added to the solution. The resulting mixture is subjected to freeze-thaw treatment twice to effect degassing, and then irradiated with the light from a 500 W high pressure mercury lamp while stirring with a magnetic stirrer. The color of the mixture gradually becomes blackish brown, and a blackish brown uniform dispersion of colloidal platinum protected by the hydrazide group-containing copolymer is obtained two hours later. Measurement of the colloidal dispersion by the use of a transmission type electron microscope (model HU-12A manufactured and sold by Hitachi Ltd., Japan) shows that the average particle diameter of the colloidal platinum particles is 40 Å, and that the colloidal platinum particles are uniformly dispersed in the dispersion.

To the colloidal platinum dispersion are added 7.215 g of a polystyrene-based weakly basic anion exchange resin [Diaion (registered trade mark) WA 20 manufactured and sold by Mitsubishi Chemical Industries, Ltd., Japan] having an apparent density of 39-45 g/l, an exchange capacity of 2.5 meg/ml or more and an effective diameter of 0.35-0.55 mm and 100 ml of phosphate buffer of pH 7 containing 024% by weight of glutaraldehyde. The resulting mixture is heated at 75° C. for 28 hours while stirring. The color of the resin gradually turns blackish brown, and the blackish brown color of the liquid phase gradually becomes pale. This indicates that the ultrafine particles of platinum are bound to the resin. Then, the resin having the platinum particles bound thereto is filtered off, sufficiently washed with water, and dried in vacuo. From the thus obtained resin, 2 g is weighed out, put in 50 g of aqua regia, and stirred at 30° C. overnight. By measuring the amount of platinum in the liquid phase using an atomic absorption spectrometer (model AA 646 manufactured and sold by Shimadzu Corporation, Japan), it is found that $1.7 \times 10^{-4}$ milligram atom of platinum particles are bound to each 1 g of the resin.

Using the thus obtained resin with ultrafine platinum particles immobilized thereonto as a catalyst, hydrogenation of cyclohexene is carried out in methanol as a solvent at 30° C. under 1 atom of hydrogen pressure. That is, to 20 ml of methanol in an eggplant type flask are added 82 mg of cyclohexene and 0.1 g of the resin with ultrafine platinum particles immobilized thereonto as obtained above, and the resulting mixture is stirred. Then, hydrogen is introduced at a pressure of 1 atom to conduct hydrogenation of the cyclohexene at 30° C. As a result, hydrogenation of the cyclohexene proceeds rapidly. The initial hydrogenation rate is 0.11 mol/sec per gram atom of the immobilized platinum.

After completion of the hydrogenation reaction, the catalyst can be readily recovered by decantation. The recovered catalyst is used again in second hydrogenation, and exhibits an activity as high as that exhibited in the first hydrogenation.

EXAMPLE 4

Substantially the same procedures as in Example 1 are repeated except that chloroauric acid ($HAuCl_4$) is used in place of potassium tetra chloroplatinate, thereby obtaining a dispersion of colloidal gold protected by a copolymer of acrylamide and N-vinyl-2-pyrrolidone having a hydrazide group. Measurement of the colloidal dispersion by the use of a transmission type electron microscope (model HU-12A manufactured and sold by Hitachi Ltd., Japan) shows that the average particle diameter of the colloidal particles is 120 Å, and that the colloidal gold particles are uniformly dispersed in the dispersion. The colloidal dispersion is very stable. That is, even when the colloidal dispersion is centrifuged at 5000 rpm for 10 min, precipitation of colloidal gold particles does not occur. Moreover, even when the colloidal dispersion is allowed to stand still at room temperature for a period of more than a month, any formation of colloidal gold precipitates is not observed.

EXAMPLE 5

The colloidal dispersion as obtained in Example 4 is acidified by addition of hydrochloric acid. To the acidified colloidal dispersion is added 1 g of a 0.5N aqueous solution of sodium nitrite. The reaction for converting the hydrazide groups of the copolymer to azide groups is conducted at 0° C. for 1 hr, thereby obtaining a dispersion of colloidal gold particles protected by a copolymer having azide groups.

Separately, 5 g of sugar mannan is reacted with 1 g of ethyleneimine at 60° C. for 3 hr to cause the mannan to have amino groups. The mannan having amino groups is added to the above obtained dispersion of colloidal gold particles protected by the copolymer having azide groups, and reacted at 20° C. for 10 hr. An aliquot of the reaction product is subjected to gel permeation chromatography using G5000PW and G3000PW columns (manufactured and sold by Toyo Soda Co., Ltd., Japan) and water as a solvent. Thus, a chromatogram is obtained, which shows a peak at a position different from those for the peaks ascribed to the animated mannan and the copolymer present, on the colloidal particles. This indicates binding of the copolymer-protected colloidal particles to the aminated mannan. Then, fractions of the product composed of aminated mannan and, bound thereto, the copolymer-protected colloidal gold particles are taken, and the fractions are subjected to elementary analysis, thereby determining the amount of the aminated mannan contained in the product. The amount of the aminated mannan is 0.02 mol per mol of the structural unit having an azide group of the copolymer.

EXAMPLE 6

Substantially the same procedures as in Example 1 are repeated except that radioactive chloroauric acid ($H^{198}AuCl_4$) is used in place of potassium tetrachloroplatinate, thereby obtaining a dispersion of radioactive colloidal gold protected by a copolymer of acrylamide and N-vinyl-2-pyrrolidone having a hydrazide group. Measurement of the colloidal dispersion by the use of a transmission type electron microscope (model HU-12A manufactured and sold by Hitachi Ltd., Japan) shows that the average particle diameter of the colloidal gold particles is 140 Å, and that the colloidal gold particles are uniformly dispersed in the dispersion. The colloidal dispersion is very stable. That is, even when the colloidal dispersion is centrifuged at 5000 rpm for 10 min, precipitation of radioactive colloidal gold particles does not occur. Moreover, even when the colloidal dispersion is allowed to stand still at room temperature for a period of more than a month, any formation of colloidal radioactive gold precipitates is not observed.

EXAMPLE 7

The colloidal dispersion as obtained in Example 6 is acidified by addition of hydrochloric acid. To the acidified colloidal dispersion is added 1 g of a 0.5N aqueous solution of sodium nitrite. The reaction for converting the hydrazide groups of the copolymer to azide groups is conducted at 0° C. for 1 hr, thereby obtaining a dispersion of colloidal radioactive gold particles protected by a copolymer having azide groups.

Separately, in substantially the same manner as described in Example 5, sugar mannan is reacted with ethyleneimine to cause the mannan to have amino groups. The mannan having amino groups is added to the above obtained dispersion of colloidal radioactive gold particles protected by the copolymer having azide groups, and reacted at 20° C. for 10 hr. An aliquot of the reaction product is subjected to gel permeation chromatography using G5000PW and G3000PW columns manufactured and sold by Toyo Soda Co., Ltd., Japan and water as a solvent. Thus, a chromatogram is obtained, which shows a peak at a position different from those for the peaks ascribed to the aminated mannan and the copolymer present on the colloidal particles. This indicates binding of the copolymer-protected colloidal particles to the aminated mannan. Then, fractions of the product composed of aminated mannan and, bound thereto, the copolymer-protected colloidal radioactive gold particles are taken, and the fractions are subjected to elementary analysis, thereby determining the amount of the aminated mannan contained in the product. The amount of the aminated mannan is 0.03 mol per mol of the structural unit having an azide group of the copolymer.

EXAMPLE 8

To 100 g of methanol are added 10 g of 1-methoxy-1-aminocarbomethylethylene and 100 mg of benzoyl peroxide. The resulting mixture is heated at 60° C. for 12 hr while stirring to obtain a polymer of the above-indicated substituted ethylene. The thus obtained polymer is reacted with hydrazine monohydrate in substantially the same manner as described in Example 1 to cause the polymer to have hydrazide groups. The hydrazide group content of this polymer is determined according to the method described in Biochemistry, vol. 8, p. 4074(1969), which is 0.63 milliequivalent per g of the polymer. Further, the molecular weight of the hydrazide group-containing polymer is determined by gel permeation chromatography in which use is made of G5000PW and G3000PW columns manufactured and sold by Toyo Soda Co., Ltd. and water as a solvent. The molecular weight is about 3,000.

Substantially the same procedures as described in Example 1 are repeated except that the above obtained polymer having hydrazide groups is employed, thereby obtaining a dispersion of colloidal platinum particles protected by the polymer. Measurement of the colloidal dispersion by the use of a transmission type electron microscope of model HU-12A manufactured and sold by Hitachi Ltd., Japan shows that the average diameter of the colloidal platinum particles is 40 Å, and that the colloidal platinum particles are uniformly dispersed in the dispersion. The colloidal dispersion is very stable. That is, even when the colloidal dispersion is centrifuged at 5000 rpm for 10 min, precipitation of colloidal platinum particles does not occur. Moreover, even when the colloidal dispersion is allowed to stand still at room temperature for a period of more than a month, any formation of colloidal platinum precipitates is not observed.

EXAMPLE 9

5 g of methyl vinyl ether and 50 g of 4-pentenamide are added to 200 g of methanol. The resulting mixture is irradiated with gamma radiation for 20 hr to copolymerize the monomers. NMR spectrum analysis of the thus-obtained copolymer shows that the 4-pentenamide content of the copolymer is 16% by mole.

Substantially the same procedures as described in Example 1 are repeated except that the above obtained copolymer is employed in place of the copolymer of acrylamdie and N-vinyl-2-pyrrolidone, to cause the copolymer to have hydrozide groups.

The hydrazide group content of this copolymer is determined according to the method described in Biochemistry, vol. 8, p. 4074(1969), which is 0.12 milliequivalent per g of the copolymer. Further, the molecular weight of the hydrazide group-containing copolymer is determined by gel permeation chromatography in which use is made of G5000PW and G3000PW columns manufactured and sold by Toyo Soda Co., Ltd. and water as a solvent. The molecular weight is about 4,500.

Substantially the same procedures as described in Example 1 are repeated except that silver nitrate is employed in place of potassium tetrachloroplatinate and that the above-obtained hydrazide group-containing copolymer is employed in place of the hydrazide group-containing copolymer of acrylamide and N-vinyl-2-pyrrolidone, thereby obtaining a dispersion of colloidal silver particles protected by the former copolymer. Measurement of the colloidal dispersion by the use of a transmission type electron microscope of model HU-12A manufactured and sold by Hitachi Ltd., Japan shows that the average diameter of the colloidal silver particles is 80 Å, and that the colloidal silver particles are uniformly dispersed in the dispersion. The colloidal dispersion is very stable. That is, even when the colloidal dispersion is centrifuged at 5000 rpm for 10 min, precipitation of colloidal silver particles does not occur. Moreover, even when the colloidal dispersion is allowed to stand still at room temperature for a period of more than a month, any formation of colloidal silver precipitates is not observed.

EXAMPLE 10

To the colloidal dispersion as obtained in Example 9 is added 1 g of a 0.5N aqueous solution of sodium nitrite. The reaction for converting the hydrazide groups of the copolymer to azide groups is conducted at 0° C. for 1 hr, thereby obtaining a dispersion of colloidal silver particles protected by a copolymer having azide groups. To the resulting dispersion is added 100 mg of albumin, followed by agitation at 10° C. overnight. An aliquot of the reaction product is subjected to gel permeation chromatography using G5000PW and G3000PW columns manufactured and sold by Toyo Soda Co., Ltd., Japan and water as a solvent. Thus, a chromatogram is obtained, which shows a peak at a position different from those for the peaks ascribed to the albumin and the copolymer present on the colloidal particles. This indicates binding of the azide copolymer-protected colloidal silver particles to the albumin. Then, fractions of the product composed of albumin and, bound thereto, the azide copolymer-protected colloidal silver particles are taken, and the fractions are subjected to amino acid analysis, thereby determining the amount of the albumin contained in the product. The amount of the albumin is 0.01 mol per mol of the structural unit having an azide group of the copolymer.

EXAMPLE 11

Substantially the same procedures as described in Example 4 are repeated, thereby obtaining a dispersion of colloidal gold protected by a copolymer of acrylamide and N-vinyl-2-pyrrolidone having a hydrazide group.

The colloidal dispersion as obtained above is acidified by addition of an aqueous hydrochloric acid solution. To the acidified colloidal dispersion is added 1 g of a 0.5N aqueous solution of sodium nitrite. The reaction for converting the hydrazide groups of the copolymer to azide groups is conducted at 0° C. for 1 hr, thereby obtaining a dispersion of colloidal gold particles protected by a copolymer having azide groups.

Substantially the same procedures as described in Example 5 are repeated except that 100 mg of concanavalin A is employed in place of the sugar mannan having an amino group incorporated thereinto, thereby causing the colloidal gold particles protected by the azide group-containing copolymer to react with the concanavalin A. An aliquot of the reaction product is subjected to gel permeation chromatography using G5000PW and G3000PW columns manufactured and sold by Toyo Soda Co., Ltd., Japan and water as a solvent. Thus, a chromatogram is obtained, which shows a peak at a position different from those for the peaks ascribed to the concanavalin A and the copolymer present on the colloidal particles. This indicates binding of the azide copolymer-protected colloidal gold particles to the concanavalin A. Then, fractions of the product composed of concanavalin A and, bound thereto, the azide copolymer-protected colloidal gold particles are taken, and the fractions are subjected to amino acid analysis, thereby determining the amount of the concanavalin A contained in the product. The amount of the concanavalin A is 0.03 mol per mol of the structural unit having an azide group of the copolymer.

EXAMPLE 12

Substantially the same procedures as described in Example 6 are repeated, thereby obtaining a dispersion of colloidal radioactive gold protected by a copolymer of acrylamide and N-vinyl-2-pyrrolidone having a hydrazide group.

The colloidal dispersion as obtained above is acidified to pH 1.0 by addition of an aqueous hydrochloric acid solution. To the acidified colloidal dispersion is added 1 g of a 0.5N aqueous solution of sodium nitrite. The reaction for converting the hydrazide groups of the copolymer to azide groups is conducted at 0° C. for 1 hr, thereby obtaining a dispersion of colloidal radioactive gold particles protected by a copolymer having azide groups.

Substantially the same procedures as described in Example 5 are repeated except that 100 mg of concanavalin A is employed in place of the sugar mannan having an amino group incorporated thereinto, thereby causing the colloidal radioactive gold particles protected by the azide group-containing copolymer to react with the concanavalin A. An aliquot of the reaction product is subjected to gel permeation chromatography using G5000PW and G3000PW columns manufactured and sold by Toyo Soda Co., Ltd., Japan and water as a solvent. Thus, a chromatogram is obtained, which shows a peak at a position different from those for the peaks ascribed to the concanavalin A and the copolymer present on the colloidal particles. This indicates binding of the azide copolymer-protected colloidal radioactive gold particles to the concanavalin A. Then, fractions of the product composed of concanavalin A and, bound thereto, the azide copolymer-protected colloidal gold particles are taken, and the fractions are subjected to amino acid analysis, thereby determining the amount of the concanavalin A contained in the product. The amount of the concanavalin A is 0.04 mol per mol of the structural unit having an azide group of the copolymer.

EXAMPLE 13

To 100 g of methanol are added 1 g of thiophenyl acrylate, 20 g of N-vinyl-2-pyrrolidone and 0.5 g of benzoyl peroxide. The resulting mixture is heated at 80° C. for 24 hr while stirring to obtain a copolymer of thiophenyl acrylate and N-vinyl-2-pyrrolidone. The thus obtained copolymer is reacted with hydrazine in substantially the same manner as described in Example 1 to cause the copolymer to have hydrazide groups. The hydrazide group content of this copolymer is determined according to the method described in Biochemistry, vol. 8, p. 4074(1969), which is 0.38 milliequivalent per g of the copolymer. Further, the molecular weight of the hydrazide group-containing copolymer is determined by gel permeation chromatography in which use is made of G5000PW and G3000PW columns manufactured and sold by Toyo Soda Co., Ltd. and water as a solvent. The molecular weight is about 25,000.

Substantially the same procedures as described in Example 1 are repeated except that the above obtained copolymer having hydrazide groups is employed, thereby obtaining a uniform blackish brown dispersion of colloidal platinum particles protected by the copolymer having hydrazide groups. Measurement of the colloidal dispersion by the use of a transmission type electron microscope of model HU-12A manufactured and sold by Hitachi Ltd., Japan shows that the average diameter of the colloidal platinum particles is 110 Å, and that the colloidal platinum particles are uniformly dispersed in the dispersion. The colloidal dispersion is very stable. That is, even when the colloidal dispersion is centrifuged at 5000 rpm for 10 min, precipitation of colloidal platinum particles does not occur. Moreover, even when the colloidal dispersion is allowed to stand still at room temperature for a period of more than a month, any formation of colloidal platinum precipitates is not observed.

EXAMPLE 14

The colloidal platinum of the dispersion as obtained in Example 13 is reacted with sodium nitrite in substantially the same manner as in Example 5, thereby obtaining a dispersion of colloidal platinum particles protected by an azide group-containing copolymer.

The colloidal platinum of the thus obtained dispersion is reacted with the aminated mannan in substantially the same manner as in Example 5. An aliquot of the reaction product is subjected to gel permeation chromatography using G5000PW and G3000PW columns manufactured and sold by Toyo Soda Co., Ltd., Japan and water as a solvent. Thus, a chromatogram is obtained, which shows a peak at a position different from those for the peaks ascribed to the aminated mannan and the copolymer present on the colloidal particles. This indicates binding of the azide copolymer-protected colloidal platinum particles to the aminated mannan. Then, fractions of the product composed of aminated mannan and, bound thereto, the azide copolymer-protected colloidal platinum particles are taken, and the fractions are subjected to elementary analysis, thereby determining the amount of the aminated mannan contained in the product. The amount of the aminated mannan is 0.04 mol per mol of the structural unit having an azide group of the copolymer.

EXAMPLE 15

To 16 ml of water are added 0.8 g of ethyl acrylate, 22 g of N-vinyl-2-pyrrolidone and 0.05 g of benzoyl peroxide. The resulting mixture is stirred at 80° C. for 12 hours to obtain a copolymer of ethyl acrylate and N-vinyl-2-pyrrolidone. Elementary analysis of the thus-obtained copolymer shows that the ethyl acrylate content of the copolymer is 32% by mole. The molecular weight of the copolymer is determined by gel permeation chromatography in which use is made of G5000PW and G3000PW columns manufactured and sold by Toyo Soda Co., Ltd. and water as a solvent. The molecular weight is about 28,000. Then, 0.11 g of the copolymer and 14.4 mg of rhodium chloride is dissolved in 50 ml of a 1:1 by volume mixed solvent of ethanol and water. The resulting solution is heated under reflux for an hour, thereby obtaining a uniform blackish brown dispersion of colloidal rhodium particles protected by the copolymer. Measurement of the colloidal dispersion by the use of a transmission type electron microscope of model HU-12A manufactured and sold by Hitachi Ltd., Japan shows that the average particle diameter of the colloidal rhodium particles is 50 Å, and that the colloidal rhodium particles are uniformly dispersed in the dispersion. The colloidal dispersion is very stable. That is, even when the colloidal dispersion is centrifuged at 5000 rpm for 10 min, precipitation of colloidal rhodium particles does not occur. Moreover, even when the colloidal dispersion is allowed to stand still at room temperature for a period of more than a month, any formation of colloidal rhodium precipitates is not found.

EXAMPLE 16

To 53 ml of water is added 1 g of a polyacrylamide gel having an aminoethyl group [Aminoethyl Bio-gel (registered trade mark) P-150 manufactured and sold by Bio Rad Laboratories, U.S.A.], and agitated for a period of 6 hours. To the mixture is added 20 ml of the colloidal rhodium dispersion as obtained in Example 15, and continued to agitate at room temperature. Three days later, the gel becomes black, while the liquid phase of the mixture becomes colorless and transparent. As a result of the atomic absorption spectroscopy of the liquid phase, no rhodium is detectable. This indicates that all of the rhodium atoms are immobilized onto the gel. Further, the rhodium-immobilized gel is subjected to elementary analysis. As a result, it is found that the colloidal rhodium is immobilized onto the gel in a proportion that 1 mol of the structural unit having an ester group of the copolymer is attached to 0.09 mole of the gel.

Even when the gel onto which the colloidal rhodium particles have been immobilized is washed with a water of pH 2 to 13 several times, any detachment of the rhodium particles from the gel is not observed.

Using the rhodium-immobilized gel as a catalyst, hydrogenation of ethyl vinyl ether, acrylonitrile, cyclohexene, mesityl oxide and 1-hexene is separately carried out in methanol as a solvent at 30° C. under 1 atom of hydrogen pressure. That is, to 20 ml of methanol in an eggplant type flask are added 0.1 g of the above-indicated compound to be hydrogenated and 0.1 g of the gel with rhodium particles immobilized thereonto as obtained above, and the resulting mixture is stirred. Then, hydrogen is introduced at a pressure of 1 atom so as to contact the compound at 30° C., thereby enabling the compound to be hydrogenated. As a result, hydrogenation of the compound proceeds rapidly. The initial hydrogenation rates for ethyl vinyl ether, acrylonitrile, cyclohexene, mesityl oxide and 1-hexene are 170, 92, 72, 56 and 75 mmol $H_2$ per gram-atom of Rh per second (mmol $H_2$/gram-atom Rh·S), respectively, which are respectively 22, 12, 10, 4.7 and 2.0 times that exhibited by the commercial catalyst available from Nippon Engelhard Ltd., Tokyo, Japan.

After completion of the hydrogenation reaction, the gel is separated by decantation. Using the thus obtained gel, hydrogenation of cyclohexene is conducted in substantially the same manner as mentioned above. The hydrogenation reaction proceeds rapidly. The initial hydrogenation rate for cyclohexene is 72 mmol $H_2$/gram-atom Rh·S, which is identical with that exhibited by the gel employed in the first hydrogenation reaction. That is, it is apparent that the colloidal rhodium-immobilized gel exhibits an excellent catalystic activity for hydrogenation, and that the gel can be repeatedly used as catalyst.

EXAMPLE 17

To 16 ml of ethanol are added 0.8 g of methyl acrylate, 22 g of N-vinyl-2-pyrrolidone and 0.05 g of benzoyl peroxide. The resulting mixture is stirred at 80° C. for 12 hours to obtain a copolymer of methyl acrylate and N-vinyl-2-pyrrolidone. Elementary analysis of the thus-obtained copolymer shows that the methyl acrylate content of the copolymer is 32% by mole. The molecular weight of the copolymer is determined by gel permeation chromatography in which use is made of G5000PW and G3000PW columns manufactured and sold by Toyo Soda Co., Ltd. and water as a solvent. The molecular weight is about 28,000. Then, 0.11 g of the copolymer and 14.4 mg of rhodium chloride is dissolved in 50 ml of a 1:1 by volume mixed solvent of ethanol and water. The resulting solution is heated under reflux for an hour, thereby obtaining a uniform blackish brown dispersion of colloidal rhodium particles protected by the copolymer. Measurement of the colloidal dispersion by the use of a transmission type electron microscope of model HU-12A manufactured and sold by Hitachi Ltd., Japan shows that the average particle diameter of the colloidal rhodium particles is 50

Å, and that the colloidal rhodium particles are uniformly dispersed in the dispersion. The colloidal dispersion is very stable. That is, even when the colloidal dispersion is centrifuged at 5000 rpm for 10 min, precipitation of colloidal rhodium particles does not occur. Moreover, even when the colloidal dispersion is allowed to stand still at room temperature for a period of more than a month, any formation of colloidal rhodium precipitates is not found.

EXAMPLE 18

The colloidal rhodium dispersion as obtained in Example 17 is immobilized onto a polyacrylamide gel having an aminoethyl group in substantially the same manner as described in Example 16. Elementary analysis of the rhodium-immobilized gel indicates that the colloidal rhodium is immobilized onto the gel in such an amount that 1 mol of the structural unit having an ester group of the copolymer is bound to 0.09 mole of the gel.

Even when the gel onto which the colloidal rhodium particles have been immobilized is washed with a water of pH 2 to 13 several times, any detachment of the rhodium particles from the gel is not observed.

Using the rhodium-immobilized gel as a catalyst, hydrogenation of ethyl vinyl ether, acrylonitrile, cyclohexene, mesityl oxide and 1-hexene is separately carried out in substantially the same manner as described in Example 16. The initial hydrogenation rates for ethyl vinyl ether, acrylonitrile, cyclohexene, mesityl oxide and 1-hexene are 170, 92, 72, 56 and 75 mmol $H_2$/gram-atom Rh·S, respectively, which are respectively 22, 12, 10, 4.7 and 2.0 times that exhibited by the commercial catalyst available from Nippon Engelhard Ltd., Tokyo, Japan.

After completion of the hydrogenation reaction, the gel is separated by decantation. Using the thus obtained gel, hydrogenation of cyclohexene is conducted in substantially the same manner as mentioned above. The hydrogenation reaction proceeds rapidly. The initial hydrogenation rate for cyclohexene is 72 mmol $H_2$/gram-atom Rh·S, which is identical with that exhibited by the gel employed in the first hydrogenation reaction. That is, it is apparent that the colloidal rhodium-immobilized gel exhibits an excellent catalytic activity for hydrogenation, and that moreover, the gel can be repeatedly used.

EXAMPLE 19

To 100 g of methanol are added 1.0 g of 4-nitrophenyl acrylate, 10 g of N-vinyl-2-pyrrolidone and 0.1 g of azobisisobutyronitrile. The resulting mixture is heated at 70° C. for 12 hours while stirring to obtain a copolymer of 4-nitrophenyl acrylate and N-vinyl-2-pyrrolidone. Elementary analysis of the thus-obtained copolymer shows taht the 4-nitrophenyl acrylate content of the copolymer is 31% by mole. The molecular weight of the copolymer is determined by gel permeation chromatography in which use is made of G5000PW and G3000PW columns manufactured and sold by Toyo Soda Co., Ltd., Japan and water as a solvent. The molecular weight is about 15,000.

0.11 g of the above obtained copolymer of 4-nitrophenyl acrylate and N-vinyl-2-pyrrolidone is dissolved in 50 ml of a 1:1 by volume mixed solvent of ethanol and water. To the resulting solution is added 5 ml of a $1.1 \times 10^{-2}$ mol/l aqueous solution of potassium tetrachloroplatinate. The mixture is subjected to freeze-thaw treatment twice to effect degassing, and then irradiated with the light from a 500 W high pressure mercury lamp for 2 hours while stirring with a magnetic stirrer to obtain a uniform blackish brown dispersion of colloidal platinum particles protected by the above-mentioned copolymer. Measurement of the colloidal dispersion by the use of a transmission type electron microscope of model HU-12A manufactured and sold by Hitachi Ltd., Japan shows that the average particle diameter of the colloidal platinum particles is 40 Å, and that the colloidal platinum particles are uniformly dispersed in the dispersion. The colloidal dispersion is very stable. That is, even when the colloidal dispersion is centrifuged at 5000 rpm for 10 min, precipitation of colloidal platinum particles does not occur. Moreover, even when the colloidal dispersion is allowed to stand still at room temperature for a period of more than a month, any formation of colloidal platinum precipitates is not found.

EXAMPLE 20

To the colloidal platinum dispersion as obtained in Example 19 is added 7.215 g of a polystyrene-based weakly basic anion exchange resin [Diaion (registered trade mark) WA 20 manufactured and sold by Mitsubishi Chemical Industries, Ltd., Japan] having an apparent density of 39-45 g/l, an exchange capacity of 2.5 meq/ml or more and an effective diameter of 0.35-0.55 mm. The resulting mixture is heated at 75° C. for 28 hours while stirring. The color of the resin gradually turns blackish brown, and the blackish brown color of the liquid phase gradually becomes clear. This indicates that the ultrafine particles of platinum are immobilized onto the resin. Then, the platinum particle-immobilized resin is filtered off, sufficiently washed with water, and dried in vacuo.

Using the resin with ultrafine platinum particles immobilized thereonto as a catalyst, hydrogenation of cyclohexene is carried out in substantially the same manner as described in Example 16. Hydrogenation of the cyclohexene proceeds rapidly. The initial hydrogenation rate is 36 mmol $H^2$/gram-atom Pt·S.

After completion of the hydrogenation reaction, the catalyst can be readily recovered by decantation. The recovered catalyst is used again in the hydrogenation under the same conditions as mentioned above, and exhibits an activity as hight as that exhibited in the first hydrogenation.

EXAMPLE 21

Substantially the same procedures as in Example 15 are repeated except that chloroauric acid ($HAuCl_4$) is used in place of rhodium chloride, thereby obtaining a dispersion of colloidal gold protected by a copolymer of methyl acrylate and N-vinyl-2-pyrrolidone. Measurement of the colloidal dispersion by the use of a transmission type electron microscope of model HU-12A manufactured and sold by Hitachi Ltd., Japan shows that the average particle diameter of the colloidal particles is 80 Å, and that the colloidal gold particles are uniformly dispersed in the dispersion. The colloidal dispersion is very stable. That is, even when the colloidal dispersion is centrifuged at 5000 rpm for 10 min, precipitation of colloidal gold particles does not occur. Moreover, even when the colloidal dispersion is allowed to stand still at room temperature for a period of more than a month, any formation of colloidal gold precipitates is not observed.

EXAMPLE 22

One g of sugar mannan is reacted with 5 g of ethyleneimine at 50° C. for 12 hr to cause the mannan to have amino groups. The mannan having amino groups is added to the colloidal gold dispersion obtained in Example 21, and the reaction is allowed to proceed at 20° C. for 10 hr.

An aliquot of the reaction product is subjected to gel permeation chromatography using G5000PW and G3000PW columns manufactured and sold by Toyo Soda Co., Ltd., Japan and water as a solvent. Thus, a chromatogram is obtained, which shows a peak at a position different from those for the peaks ascribed to the aminated mannan and the polymer present on the colloidal particles. This indicates binding to the aminated mannan of the colloidal particles protected by the copolymer of N-vinyl-2-pyrrolidone and methyl acrylate. Then, fractions of the products are taken, and the fractions are subjected to elementary analysis, thereby determining the proportion of the aminated mannan contained in the products. The proportion is 0.06 mol per mol of the structural unit having an ester group of the polymer.

EXAMPLE 23

Substantially the same procedures as in Example 15 are repeated except that radioactive chloroauric acid ($H^{198}AuCl_4$) is used in place of rhodium chloride, thereby obtaining a dispersion of radioactive gold protected by a copolymer of methyl acrylate and N-vinyl-2-pyrrolidone. Measurement of the dispersion by the use of a transmission type electron microscope of model HU-12A manufactured and sold by Hitachi Ltd., Japan shows that the average particle diameter of the colloidal gold is 70 Å, and that the colloidal radioactive gold particles are uniformly dispersed in the dispersion. The dispersion is very stable. That is, even when the dispersion is centrifuged at 5000 rpm for 10 min, precipitation of colloidal radioactive gold particles does not occur. Moreover, even when the dispersion is allowed to stand still at room temperature for a period of more than a month, any formation of colloidal radioactive gold precipitates is not observed.

EXAMPLE 24

To 100 g of methanol are added 10 g of N-vinyl-2-pyrrolidone and 1 g of 2,2,2-trifluoroethyl acrylate. To the resulting mixture is added 0.1 g of azobisisobutyronitrile, followed by stirring at 70° C. for 12 hours to conduct copolymerization. Elementary analysis of the thus obtained copolymer shows that the 2,2,2-trifluoroethyl acrylate content is 28 mol %. The molecular weight of the copolymer obtained is determined by gel permeation chromatography in which use is made of G5000PW and G3000PW columns manufactured and sold by Toyo Soda Co., Ltd. and water as a solvent. The molecular weight is about 25,000.

Substantially the same procedures as in Example 19 are repeated except that silver nitrate and the above-obtained copolymer are respectively used in place of potassium tetrachloroplatinate and the copolymer of 4-nitrophenyl acrylate and N-vinyl-2-pyrrolidone, to obtain a copolymer-protected colloidal silver dispersion. Measurement of the colloidal dispersion by the use of a transmission type electron microscope of model HU-12A manufactured and sold by Hitachi Ltd., Japan shows that the average particle diameter of the colloidal silver particles is 40 Å, and that the colloidal silver particles are uniformly dispersed in the dispersion. The colloidal dispersion is very stable. That is, even when the colloidal dispersion is centrifuged at 5000 rpm for 10 min, precipitation of the colloidal silver particles does not occur. Moreover, even when the colloidal dispersion is allowed to stand still at room temperature for a period of more than a month, precipitation of the colloidal silver particles is not observed.

EXAMPLE 25

To the colloidal silver dispersion obtained in Example 24 is added 100 mg of albumin, followed by stirring at 10° C. overnight. An aliquot of the reaction mixture is subjected to gel permeation chromatography using G5000PW and G3000PW columns manufactured and sold by Toyo Soda Co., Ltd., Japan and water as a solvent. As a result, it is found that there is observed a peak at a position different from those for the peaks ascribed to the albumin and the copolymer present in the colloidal silver dispersion. This indicates that the colloidal silver particles protected by the copolymer are bound to the albumin. Then, fractions of the resultant is taken, and subjected to amino acid analysis to determine the proportion of the albumin contained therein. The proportion is 0.05 mol per mol of the structural units having an ester group of the copolymer.

EXAMPLE 26

Substantially the same procedures as in Example 15 are repeated except that chloroauric acid ($HAuCl_4$) is used in place of rhodium chloride to obtain a colloidal gold dispersion in which the colloidal gold particles are protected by a copolymer of ethyl acrylate and N-vinyl-2-pyrrolidone. Measurement of the colloidal dispersion by the use of a transmission type electron microscope of model HU-12A manufactured and sold by Hitachi Ltd., Japan shows that the average particle diameter of the colloidal gold particles is 80 Å, and that the colloidal gold particles are uniformly dispersed in the dispersion. The colloidal dispersion is very stable. That is, even when the colloidal dispersion is centrifuged at 5000 rpm for 10 min, precipitation of colloidal gold particles does not occur. Moreover, even when the colloidal dispersion is allowed to stand still at room temperature for a period of more than a month, any formation of colloidal gold precipitates is not observed.

EXAMPLE 27

Using the dispersion obtained in Example 26, substantially the same procedures as in Example 22 are repeated except that 100 mg of concanavalin A is used instead of the aminated mannan, to effect the reaction between concanavalin A and the dispersion in which the colloidal gold particles are protected by the copolymer of ethyl acrylate and N-vinyl-2-pyrrolidone. An aliquot of the reaction mixture is subjected to gel permeation chromatography using G5000PW and G3000PW columns manufactured and sold by Toyo Soda Co., Ltd., Japan and water as a solvent. As a result, it is found that there is observed a peak at a position different from those for the peaks ascribed to the concanavalin A and the copolymer present in the colloidal gold dispersion. This indicates that the colloidal gold particles protected by the copolymer are bound to the concanavalin A. Then, fractions of the resultant is taken, and subjected to amino acid analysis to determine the proportion of the concanavalin A contained therein.

The proportion is 0.08 mol per mol of the structural units having an ester group of the copolymer.

EXAMPLE 28

To 100 g of methanol are added 10 g of methyl vinyl ether and 1 g of methacrylic acid. To the resulting mixture is added 0.1 g of benzoyl peroxide, followed by stirring at 80° C. for 12 hours to obtain a copolymer. 1 g of the copolymer obtained is refluxed with 10 g of thionyl chloride for 8 hr to convert the carboxyl groups in the copolymer into acid chloride groups. Then, 1 g of the thus obtained copolymer and 1 g of 4-nitrophenol are added to 10 ml of pyridine, and refluxed for 2 hr to obtain a copolymer having 4-nitrophenyl ester groups. Elementary analysis of the thus obtained copolymer shows that the 4-nitrophenyl acrylate content is 32 mol %. The molecular weight of the above-obtained copolymer is determined by gel permeation chromatography using G5000PW and G3000PW columns manufactured and sold by Toyo Soda Co., Ltd., Japan and water as a solvent. The molecular weight is about 55,000.

Substantially the same procedures as in Example 15 are repeated except that the above-obtained 4-nitrophenylester-containing copolymer is used in place of the copolymer of N-vinyl-2-pyrrolidone and ethyl acrylate, thereby to obtain a colloidal dispersion of rhodium particles protected by the copolymer.

Measurement of the colloidal dispersion by the use of a transmission type electron microscope of model HU-12A manufactured and sold by Hitachi Ltd., Japan shows that the average particle diameter of the colloidal rhodium particles is 25 Å, and that the colloidal rhodium particles are uniformly dispersed in the dispersion. The colloidal dispersion is very stable. That is, even when the colloidal dispersion is centrifuged at 5000 rpm for 10 min, precipitation of the colloidal rhodium particles does not occur. Moreover, even when the colloidal dispersion is allowed to stand still at room temperature for a period of more than a month, any formation of the colloidal rhodium precipitates is not found.

EXAMPLE 29

To 100 g of methanol are added 1 g of thiophenyl acrylate, 10 g of N-vinyl-2-pyrrolidone and 0.1 g of benzoyl peroxide. The resulting mixture is heated at 80° C. while stirring for 12 hours, thereby to obtain a copolymer of thiophenyl acrylate and N-vinyl-2-pyrrolidone.

Elementary analysis of the thus obtained copolymer shows that the thiophenyl acrylate content of the copolymer is 36% by mole. Further, the molecular weight of the above-obtained copolymer is determined by gel permeation chromatography using G5000PW and G3000PW columns manufactured and sold by Toyo Soda Co., Ltd., Japan and water as a solvent. The molecular weight is about 35,000.

Substantially the same procedures as described in Example 15 are repeated except that the above-obtained copolymer is used in place of the copolymer obtained in Example 15, thereby to obtain a uniform blackish brown dispersion of colloidal rhodium protected by the copolymer. Measurement of the colloidal dispersion by the use of a transmission type electron microscope of model HU-12A manufactured and sold by Hitachi Ltd., Japan shows that the average particle diameter of the colloidal rhodium particles is 25 Å, and that the colloidal rhodium particles are uniformly dispersed in the dispersion. The colloidal dispersion is very stable. That is, even when the colloidal dispersion is centrifuged at 5000 rpm for 10 min, precipitation of colloidal rhodium particles does not occur. Moreover, even when the dolloidal dispersion is allowed to stand still at room temperature for a period of more than a month, any formation of colloidal rhodium precipitates is not observed.

EXAMPLE 30

A colloidal rhodium dispersion in which the rhodium particles are protected by a copolymer of thiophenyl acrylate and N-vinyl-2-pyrrolidone is obtained in substantially the same manner as described in Example 29. The thus obtained colloidal rhodium dispersion is reacted with aminated mannan in substantially the same manner as described in Example 22 except that the above-obtained colloidal rhodium dispersion is used in place of the colloidal gold dispersion.

An aliquot of the reaction product is subjected to gel permeation chromatography using G5000PW and G3000PW columns manufactured and sold by Toyo Soda Co., Ltd., Japan and water as a solvent. Thus, a chromatogram is obtained, which shows a peak at a position different from those for the peaks ascribed to the aminated mannan and the copolymer present on the colloidal particles. This indicates binding of the above-obtained colloidal particles protected by the copolymer of thiophenyl acrylate and N-vinyl-2-pyrrolidone to the aminated mannan. Then, fractions of the product composed of aminated mannan and, bound thereto, the copolymer-protected colloidal rhodium particles are taken, and the fractions are subjected to elementary analysis, thereby determining the amount of the aminated mannan contained in the product. The amount of the aminated mannan is 0.08 mol per mol of the structural unit having an ester group of the copolymer.

EXAMPLE 31

To 100 g of water are added 1 g of acrylamide, 10 g of methyl vinyl ketone and 0.1 g of benzoyl peroxide. The resulting mixture is stirred at 80° C. for 12 hours to obtain a copolymer of acrylamide and methyl vinyl ketone. NMR spectrum analysis of the thus obtained copolymer shows that the acrylamide content of the copolymer is 28% by mole. Further, the molecular weight of the above-obtained copolymer is determined by gel permeation chromatography using G5000PW and G3000PW columns manufactured and sold by Toyo Soda Co., Ltd., Japan and water as a solvent. As a result, it is found that the molecular weight of the copolymer is about 32,000.

0.1 g of the copolymer is dissolved in 50 ml of a mixture of ethanol and water (1:1 by volume). To the resulting mixture is added 5 ml of a $1.1 \times 10^{-2}$ mol/l of aqueous solution of potassium tetrachloroplatinate. The mixture is subjected to freeze-thraw treatment twice to effect degassing, and then irradiated with the light from a 500 W high pressure mercury lamp for 2 hours while stirring with a magnetic stirrer to obtain a uniform blackish brown dispersion of colloidal platinum particles protected by the copolymer. Measurement of the colloidal platinum dispersion by the use of a transmission type electron microscope of model HU-12A manufactured and sold by Hitachi Ltd., Japan shows that the average particle diameter of the colloidal platinum is 40 Å, and that the colloidal platinum particles are uniformly dispersed in the dispersion. The colloidal platinum dispersion is very stable. That is, even when the colloidal platinum dispersion is centrifuged at 5000 rpm for 10 min, precipitation of platinum particles does not occur. Moreover, even when the colloidal platinum dispersion is allowed to stand at room temperature for a period of more than one month, any formation of precipitates of platinum particles is not found.

EXAMPLE 32

1 g of an aminoethylated polyacrylamide gel (manufactured and sold by Bio-Rad Laboratories, U.S.A., the amount of aminoethyl residue in a dry state: 1.74 meq/g) is added to 50 ml of water and allowed to swell in water to obtain a gel mixture. Separately, to the colloidal platinum dispersion obtained in Example 31 is added hydrochloric acid to adjust the pH value of the dispersion to 5. 20 ml of the resulting colloidal platinum dispersion is added to the above-obtained gel mixture. The mixture is stirred at 20° C. so that the color of the gel is gradually getting blackish brown, and the blackish brown color of the liquid phase of the mixture is gradually getting clear. This indicates that the colloidal platinum particles are being immobilized onto the gel. Three days later, the color of the liquid phase becomes transparent, indicating that the colloidal particles have completely been immobilized onto the gel. Then, the resultant is filtered off, sufficiently washed with water, and dried in vacuo. The resulting dried gel is subjected to measurement of the amount of platinum particles immobilized onto the gel in substantially the same manner as in Example 3. As a result, it is found that the amount of platinum particles immobilized onto the gel is $2.0 \times 10^{-2}$ milligram-atom per g of the gel.

Using as a catalyst the thus obtained gel having immobilized thereonto platinum particles, hydrogenation of cyclohexene is carried out in methanol as a solvent at 30° C. under 1 atm of hydrogen gas pressure. That is, to 20 ml of methanol in an eggplant type flask are added 86 mg of cyclohexene and 0.1 g of the gel having immobilized thereonto platinum particles obtained above, and the resulting mixture is stirred. Then, hydrogen gas is introduced at a pressure of 1 atm to conduct hydrogenation of the cyclohexene at 30° C. The hydrogenation of the cyclohexene proceeds rapidly. The initial hydrogenation rate is 0.20 mol/gram-atom of Pt per sec.

After completion of the hydrogenation reaction, the catalyst is readily recovered by decantation. The recovered catalyst exhibits an activity as high as that exhibited in the first hydrogenation.

EXAMPLE 33

Substantially the same procedures as in Example 31 are repeated to obtain a colloidal platinum dispersion in which the platinum particles are protected by a copolymer of acrylamide and methyl vinyl ketone. The pH value of the colloidal platinum dispersion is adjusted to 5 by adding hydrochloric acid. To the resulting dispersion are added 7.215 g of a polystyrene-based weakly basic anion exchange resin [Diaion (trade mark) WA 20 manufactured and sold by Mitsubishi Chemical Industries, Ltd., Japan] having an apparent density of 39-45 g/l, an exchange capacity of 2.5 meq/ml or more and an effective diameter of 0.35-0.55 mm and 100 ml of phosphate buffer of pH 7 containing 0.24% by weight of glutaraldehyde. The resulting mixture is heated at 75° C. for 28 hours while stirring. The color of the resin gradually turns blackish brown, and the blackish brown color of the liquid phase gradually becomes clear. This indicates that the colloidal platinum particles are immobilized onto the resin. Then, the resultant resin is filtered off, sufficiently washed with water, and dried in vacuo. From the dried resin having immobilized thereonto platinum particles, 2 g is weighed out, put in 50 g of aqua regia, and stirred at 30° C. overnight. The liquid phase of the resulting mixture is taken out of the mixture and subjected to measurement of the amount of platinum particles immobilized onto the gel in substantially the same manner as in Example 3. As a result, it is found that the amount of platinum immobilized onto the gel is $1.0 \times 10^{-4}$ milligram-atom per g of the gel.

Using as a catalyst the thus obtained gel having immobilized thereonto platinum particles, hydrogenation of cyclohexene is carried out in methanol as a solvent at 30° C. under 1 atm of hydrogen gas pressure. That is, to 20 ml of methanol in an eggplant type flask are added 86 mg of cyclohexene and 0.1 g of the gel having immobilized threonto platinum particles obtained above, and the resulting mixture is stirred. Then, hydrogen gas is introduced at a pressure of 1 atm to conduct hydrogenation of the cyclohexene at 30° C. The hydrogenation of the cyclohexene proceeds rapidly. The initial hydrogenation rate is 0.11 mol/gram-atom of Pt per sec.

After completion of the hydrogenation reaction, the catalyst is readily recovered by decantation. The recovered catalyst is used again in the hydrogenation under the same conditions as mentioned above, and exhibits an activity as high as that exhibited in the first hydrogenation.

EXAMPLE 34

Substantially the same procedures as in Example 31 are repeated except that chloroauric acid (HAuCl$_4$) is used in place of potassium tetrachloroplatinate, thereby obtaining a dispersion of colloidal gold particles protected by a copolymer of acrylamide and methyl vinyl ketone. Measurement of the colloidal gold dispersion by the use of a transmission type electron microscope of model HU-12A manufactured and sold by Hitachi Ltd., Japan shows that the average particle diameter of the colloidal particles is 80 Å, and that the colloidal gold particles are uniformly dispersed in the dispersion. The colloidal gold dispersion is very stable. That is, even when the colloidal gold dispersion is centrifuged at 5000 rpm for 10 min, precipitation of gold particles does not occur. Moreover, even when the colloidal gold dispersion is allowed to stand at room temperature for a period of more than one month, any formation of precipitates of gold particles is not found.

EXAMPLE 35

To the colloidal gold dispersion obtained in Example 34 is added hydrochloric acid to adjust the pH value of the colloidal gold dispersion to 5.

Separately, 1 g of sugar mannan is reacted with 5 g of ethyleneimine at 50° C. for 12 hr to introduce amino groups to mannan. The thus obtained mannan having amino groups is added to the above-obtained colloidal gold dispersion, and the reaction is allowed to proceed at 20° C. for 10 hr. An aliquot of the reaction mixture is subjected to gel permeation chromatography using G5000PW and G3000PW columns manufactured and sold by Toyo Soda Co., Ltd., Japan and water as a solvent. As a result, it is found that there is observed a peak at a position different from those for the peaks ascribed to the aminated mannan and the copolymer present on the colloidal gold particles. This indicates that the colloidal gold particles protected by the copolymer of acrylamide and methyl vinyl ketone are bound to the aminated mannan. Then, fractions of the product composed of aminated mannan and, bound thereto, the copolymer-protected colloidal gold particles are taken, and the fractions are subjected to elementary analysis, thereby determining the amount of the aminated mannan contained in the product. The amount of the aminated mannan is 0.06 mol per mol of the structural unit having an amide group of the copolymer.

EXAMPLE 36

Substantially the same procedures as in Example 31 are repeated except that radioactive chloroauric acid ($H^{198}AuCl_4$) is used in place of potassium tetrachloroplatinate, thereby obtaining a dispersion of colloidal ratioactive gold particles protected by a copolymer of acrylamide and methyl vinyl ketone. Measurement of the colloidal gold dispersion by the use of a transmission type electron microscope of model HU-12A manufactured and sold by Hitachi Ltd., Japan shows that the average particle diameter of the colloidal gold particles is 90 Å, and that the colloidal gold particles are uniformly dispersed in the dispersion. The colloidal gold dispersion is very stable. That is, even when the colloidal gold dispersion is centrifuged at 5000 rpm for 10 min, precipitation of radioactive gold particles does not occur. Moreover, even when the colloidal gold dispersion is allowed to stand at room temperature for a period of more than one month, any formation of radioactive gold precipitates is not observed.

EXAMPLE 37

To the colloidal gold dispersion obtained in Example 36 is added hydrochloric acid to adjust the pH value of the colloidal gold dispersion to 5.

Separately, 1 g of sugar mannan is reacted with 5 g of ethyleneimine at 50° C. for 12 hr to introduce amino groups to mannan. The thus obtained mannan having amino groups is added to the above-obtained colloidal gold dispersion, and the reaction is allowed to proceed at 20° C. for 10 hr. An aliquot of the reaction mixture is subjected to gel permeation chromatography using G5000PW and G3000PW columns manufactured and sold by Toyo Soda Co., Ltd., Japan and water as a solvent. As a result, it is found that there is observed a peak at a position different from those for the peaks ascribed to the aminated mannan and the copolymer present on the colloidal gold particles. This indicates that the colloidal gold particles protected by the copolymer of acrylamide and methyl vinyl ketone are bound to the aminated mannan. Then, fractions of the product composed of aminated mannan and, bound thereto, the copolymer-protected colloidal gold particles are taken, and the fractions are subjected to elementary analysis, thereby determining the amount of the aminated mannan contained in the product. The amount of the aminated mannan is 0.06 mol per mol of the structural unit having an amide group of the copolymer.

EXAMPLE 38

To 100 g of a mixture of water and methanol (1:1 by volume) are added 1 g of acrylamide, 10 g of methyl vinyl ether and 0.1 g of benzoyl peroxide. The resulting mixture is stirred at 60° C. for 12 hours to obtain a copolymer of acrylamide and methyl vinyl ether. NMR spectrum analysis of the thus obtained copolymer shows that the acrylamide content of the copolymer is 34% by mole. Further, the molecular weight of the above-obtained copolymer is determined by gel permeation chromatography using G5000PW and G3000PW columns manufactured and sold by Toyo Soda Co., Ltd., Japan and water as a solvent. As a result, it is found that the molecular weight of the copolymer is about 35,000.

Substantially the same procedures as in Example 31 are repeated except that the above-obtained copolymer is used instead of the copolymer of acrylamide and methyl vinyl ketone, to obtain a dispersion of colloidal platinum particles protected by the copolymer of acrylamide and methyl vinyl ether. The colloidal platinum dispersion is very stable. That is, even when the colloidal platinum dispersion is centrifuged at 5000 rpm for 10 min, precipitation of platinum particles does not occur. Moreover, even when the colloidal platinum dispersion is allowed to stand at room temperature for a period of more than one month, any formation of precipitates of platinum particles is not found.

EXAMPLE 39

To 100 g of a mixture of water and methanol (1:1 by volume) are added 1 g of methacrylamide, 10 g of methyl vinyl ether and 0.1 g of benzoyl peroxide. The resulting mixture is stirred at 80° C. for 12 hours to obtain a copolymer of methacrylamide and methyl vinyl ether.

Substantially the same procedures as in Example 31 are repeated except that the above-obtained copolymer is used instead of the copolymer of acrylamide and methyl vinyl ketone and that silver nitrate is used instead of potassium tetrachloroplatinate, to obtain a dispersion of colloidal silver particles protected by the copolymer of acrylamide and methyl vinyl ether. Measurement of the thus obtained colloidal silver dispersion by the use of a transmission type electron microscope of model HU-12A manufactured and sold by Hitachi Ltd., Japan shows that the average particle diameter of the colloidal silver is 80 Å, and that the colloidal silver particles are uniformly dispersed in the dispersion. The colloidal silver dispersion is very stable. That is, even when the colloidal silver dispersion is centrifuged at 5000 rpm for 10 min, precipitation of silver particles does not occur. Moreover, even when the colloidal silver dispersion is allowed to stand at room temperature for a period of more than one month, any formation of precipitates of silver particles is not found.

EXAMPLE 40

To the colloidal silver dispersion obtained in Example 39 is added hydrochloric acid to adjust the pH value of the colloidal silver dispersion to 5. To the resulting colloidal silver dispersion is added 100 mg of albumin, followed by stirring at 10° C. overnight. An aliquot of the reaction mixture is subjected to gel permeation chromatography using G5000PW and G3000PW columns manufactured and sold by Toyo Soda Co., Ltd., Japan and water as a solvent. As a result, it is found that there is observed a peak at a position different from those for the peaks ascribed to the albumin and the copolymer present on the colloidal silver dispersion particles. This indicates that the colloidal silver particles protected by the copolymer of acrylamide and methyl vinyl ether are bound to the albumin. Then, fractions of the product composed of albumin and, bound thereto, the copolymer-protected colloidal silver particles are taken, and the fractions are subjected to elementary analysis, thereby determining the amount of the albumin contained in the product. The amount of the albumin is 0.09 mol per mol of the structural unit having an amide group of the copolymer.

EXAMPLE 41

Substantially the same procedures as in Example 31 are repeated except that chloroauric acid ($HAuCl_4$) is used in place of potassium tetrachloroplatinate, thereby obtaining a dispersion of colloidal gold particles protected by a copolymer of acrylamide and methyl vinyl ketone. Measurement of the colloidal gold dispersion by the use of a transmission type electron microscope of model HU-12A manufactured and sold by Hitachi Ltd., Japan shows that the average particle diameter of the colloidal particles is 80 Å, and that the colloidal gold particles are uniformly dispersed in the dispersion. The colloidal gold dispersion is very stable. That is, even when the colloidal gold dispersion is centrifuged at 5000 rpm for 10 min, precipitation of gold platinum particles does not occur. Moreover, even when the colloidal gold dispersion is allowed to stand at room temperature for a period of more than one month, any formation of precipitates of gold particles is not found.

Substantially the same procedures as in Example 35 are repeated except that 100 mg of concanavalin A is used instead of the aminated mannan, thereby to advance a reaction between concanavalin A and colloidal gold particles protected by the copolymer of acrylamide and methyl vinyl ketone. An aliquot of the reaction mixture is subjected to gel permeation chromatography using G5000PW and G3000PW columns manufactured and sold by Toyo Soda Co., Ltd., Japan and water as a solvent. As a result, it is found that there is observed a peak at a position different from those for the peaks ascribed to the concanavalin A and the copolymer present on the colloidal gold particles. This indicates that the colloidal gold particles protected by the copolymer of acrylamide and methyl vinyl ketone are bound to the concanavalin A. Then, fractions of the product composed of concanavalin A and, bound thereto, the copolymer-protected colloidal gold particles are taken, and the fractions are subjected to elementary analysis, thereby determining the amount of the concanavalin A contained in the product. The amount of the concanavalin A is 0.02 mol per mol of the structural unit having an amide group of the copolymer.

EXAMPLE 42

Substantially the same procedures as in Example 36 are repeated to obtain a dispersion of colloidal radioactive gold particles protected by a copolymer of acrylamide and methyl vinyl ketone.

Substantially the same procedures as in Example 35 are repeated except that 100 mg of concanavalin A is used instead of the aminated mannan, thereby to advance a reaction between concanavalin A and colloidal radioactive gold particles protected by the copolymer of acrylamide and methyl vinyl ketone. An aliquot of the reaction mixture is subjected to gel permeation chromatography using G5000PW and G3000PW columns manufactured and sold by Toyo Soda Co., Ltd., Japan and water as a solvent. As a result, it is found that there is observed a peak at a position different from those for the peaks ascribed to the concanavalin A and the copolymer present on the colloidal gold particles. This indicates that the colloidal radioactive gold particles protected by the copolymer of acrylamide and methyl vinyl ketone are bound to the concanavalin A. Then, fractions of the product composed of concanavalin A and, bound thereto, the copolymer-protected colloidal radioactive gold particles are taken, and the fractions are subjected to elementary analysis, thereby determining the amount of the concanavalin A contained in the product. The amount of the concanavalin A is 0.04 mol per mol of the structural unit having an amide group of the copolymer.

EXAMPLE 43

Substantially the same procedures as in Example 34 are repeated to obtain a dispersion of colloidal gold particles protected by a copolymer of acrylamide and methyl vinyl ketone.

Substantially the same procedures as in Example 35 are repeated except that 100 mg of concanavalin A is used instead of the aminated mannan, thereby to advance a reaction between concanavalin A and colloidal gold particles protected by the copolymer of acrylamide and methyl vinyl ketone. An aliquot of the reaction mixture is subjected to gel permeation chromatography using G5000PW and G3000PW columns manufactured and sold by Toyo Soda Co., Ltd., Japan and water as a solvent. As a result, it is found that there is observed a peak at a position different from those for the peaks ascribed to the concanavalin A and the copolymer present on the colloidal gold particles. This indicates that the colloidal gold particles protected by the copolymer of acrylamide and methyl vinyl ketone are bound to the concanavalin A. Then, fractions of the product composed of concanavalin A and, bound thereto, the copolymer-protected colloidal gold particles are taken, and the fractions are subjected to elementary analysis, thereby determining the amount of the concanavalin A contained in the product. The amount of the concanavalin A is 0.02 mol per mol of the structural unit having an amide group of the copolymer.

EXAMPLE 44

Substantially the same procedures as in Example 36 are repeated to obtain a dispersion of colloidal radioactive gold particles protected by a copolymer of acrylamide and methyl vinyl ketone.

Substantially the same procedures as in Example 37 are repeated except that 100 mg of concanavalin A is used instead of the aminated mannan, thereby to advance a reaction between concanavalin A and colloidal radioactive gold particles protected by the copolymer of acrylamide and methyl vinyl ketone. An aliquot of the reaction mixture is subjected to gel permeation chromatography using G5000PW and G3000PW columns manufactured and sold by Toyo Soda Co., Ltd., Japan and water as a solvent. As a result, it is found that there is observed a peak at a position different from those for the peaks ascribed to the concanavalin A and the copolymer present on the colloidal gold particles. This indicates that the colloidal radioactive gold particles protected by the copolymer of acrylamide and methyl vinyl ketone are bound to the concanavalin A. Then, fractions of the product composed of concanavalin A and, bound thereto, the copolymer-protected colloidal radioactive gold particles are taken, and the fractions are subjected to elementary analysis, thereby determining the amount of the concanavalin A contained in the product. The amount of the concanavalin A is 0.04 mol per mol of the structural unit having an amide group of the copolymer.

What is claimed is:

1. A polymer-protected colloidal metal dispersion comprising:
   (a) a polar dispersion medium selected from the group consisting of water, a mixture of water and at least one lower alcohol and a mixture of water and a water-miscible ether;
   (b) colloidal particles of at least one metal selected from the group consisting of metals belonging to Groups Ib, VIIb and VIII of the Periodic Table, said colloidal particles having an average size of less than 500 Å being dispersed in said dispersion medium; and
   (c) a protective polymer adsorbed on each of said colloidal particles;
   said protective polymer comprising 1 to 100 mol percent, based on the total of units (i), (ii) and (iii), of units (i) represented by the formula [I]

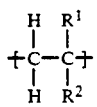

wherein
   $R^1$ is selected from the group consisting of a hydrogen atom, a substituted or unsubstituted alkyl group having 1 to 6 carbon atoms, a substituted or unsubstituted phenyl group, a hydroxyl group,

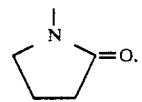

—CO—R and —O—R',
   wherein
   R is selected from the group consisting of a substituted or unsubstituted alkyl group having 1 to 10 carbon atoms and —$(CH_2)_{n1}$—$X_{n2}$—$(CH_2)_{n3}$—$Y_{n4}$—$(CH_2)_{n5}$—CO—$R^7$,
   wherein
   X and Y are each independently selected from the group consisting of —O— and —NH—,
   $R^7$ is selected from the group consisting of —NH—$NH_2$, —A—$R^8$ and —$NH_2$,
   wherein
   A is selected from the group consisting of —O— and —S—, and
   $R^8$ is selected from the group consisting of a substituted or unsubstituted alkyl group having 1 to 10 carbon atoms, a substituted or unsubstituted phenyl group and a substituted or unsubstituted succinimido group,
   n1, n3 and n5 each independently represent an integer of 0 to 6, and
   n2 and n4 each independently represent an integer of 0 or 1, and
   R' has the same meaning as R, and
   $R^2$ represents —$(CH_2)_{n1'}$—$X'_{n2'}$—$(CH_2)_{n3'}$—$Y'_{n4'}$—$(CH_2)_{n5'}$—CO—$R^{7'}$
   wherein
   X', Y', $R^{7'}$, n1', n2', n3', n4' and n5' respectively have the same meanings as X, Y, $R^7$, n1, n2, n3, n4 and n5;
   0 to 99 mol percent, based on the total of units (i), (ii) and (iii), of units (ii) represented by the formula [II]

wherein
   $R^3$ is selected from the group consisting of a hydrogen atom, a substituted or unsubstituted alkyl group having 1 to 6 carbon atoms, a substituted or unsubstituted phenyl group, a hydroxyl group,

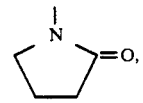

—CO—R and —O—R'
   wherein
   R and R' are as defined above, and
   $R^4$ represents —$(CH_2)_{n1''}$—$X''_{n2''}$—$(CH_2)_{n3''}$—$Y''_{n4''}$—$(CH_2)_{n5''}$—CO—$R^9$
   wherein
   X'', Y'', n1'', n2'', n3'', n4'' and n5'' respectively have the same meanings as X, Y, n1, n2, n3, n4 and n5, and
   $R^9$ represents —A'—$R^{10}$,
   wherein
   A' has the same meaning as A, and
   $R^{10}$ is selected from the group consisting of a hydrogen atom, an alkali metal, an alkaline earth metal, a substituted or unsubstituted alkyl group having 1 to 10 carbon atoms, a substituted or unsubstituted phenyl group and a substituted or unsubstituted succinimido group; and
   0 to 99 mol percent, based on the total of units (i), (ii) and (iii), of units (iii) represented by the formula [III]

wherein
   $R^5$ is selected from the group consisting of a hydrogen atom, a substituted or unsubstituted alkyl group having 1 to 6 carbon atoms, a substituted or unsubstituted phenyl group, a hydroxyl group,

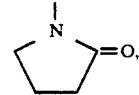

—CO—R and —O—R'
   wherein
   R and R' are as defined above, and
   $R^6$ is selected from the group consisting of a hydroxyl group

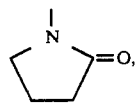

—CO—R and —O—R'
wherein
R and R' are as defined above;
provided that
where
$R^1$ is a hydrogen atom, $R^2$ is —CO—$NH_2$ and the proportion of units (ii) is 0 mol percent, $R^6$ is selected from the group consisting of a hydroxyl group, —CO—R and —O—R';
where
$R^7$ is —NH—$NH_2$, the —NH—$NH_2$ groups are unmodified, or part or all of the —NH—$NH_2$ groups are modified to form —$N_3$ groups; and
where
$R^1$ is a hydrogen atom or a substituted or unsubstituted alkyl group having 1 to 6 carbon atoms, the proportions of units (i), (ii) and (iii) are respectively 1 to 95 mol percent, 0 to 90 mol percent and 5 to 99 mol percent, based on the total of units (i), (ii) and (iii).

2. The colloidal metal dispersion according to claim 1, wherein $R^7$ is —NH—$NH_2$.

3. The colloidal metal dispersion according to claim 1, wherein $R^7$ is —A—$R^8$ wherein A and $R^8$ are as defined above.

4. The colloidal metal dispersion according to claim 1, wherein $R^7$ is —$NH_2$.

5. The colloidal metal dispersion according to claim 1, wherein said colloidal particles are of at least one metal selected from the group consisting of gold, silver, platinum, ruthenium, rhodium, palladium, osmium, rhenium, iridium, copper and nickel.

6. The colloidal metal dispersion according to claim 5, wherein said colloidal particles are of at least one metal selected from the group consisting of radioactive gold, radioactive silver and radioactive platinum.

* * * * *

UNITED STATES PATENT AND TRADEMARK OFFICE
CERTIFICATE OF CORRECTION

PATENT NO.: 5,187,209
DATED : February 16, 1993
INVENTOR(S): HIRAI et al

It is certified that error appears in the above-identified patent and that said Letters Patent is hereby corrected as shown below:

Column 49, claim 1, line 2, delete "polymer-protected colloidal" and insert --protective colloid polymer--;

Column 49, claim 1, line 13, after "protective" insert --colloid--;

Column 49, claim 1, line 15, after "protective" insert --colloid--.

Signed and Sealed this

Twenty-sixth Day of July, 1994

Attest:

BRUCE LEHMAN

*Attesting Officer*  *Commissioner of Patents and Trademarks*